United States Patent
Hirschel et al.

(10) Patent No.: US 9,902,928 B2
(45) Date of Patent: Feb. 27, 2018

(54) BIOMANUFACTURING SUITE AND METHODS FOR LARGE-SCALE PRODUCTION OF CELLS, VIRUSES, AND BIOMOLECULES

(71) Applicant: BIOVEST INTERNATIONAL, INC., Tampa, FL (US)

(72) Inventors: Mark Hirschel, Blaine, MN (US); Robert J. Wojciechowski, Forest Lake, MN (US); Kim Arneson, Minneapolis, MN (US)

(73) Assignee: BIOVEST INTERNATIONAL, INC., Tampa, FL (US)

( * ) Notice: Subject to any disclaimer, the term of this patent is extended or adjusted under 35 U.S.C. 154(b) by 0 days.

(21) Appl. No.: 14/424,944

(22) PCT Filed: Aug. 28, 2013

(86) PCT No.: PCT/US2013/057156
§ 371 (c)(1),
(2) Date: Feb. 27, 2015

(87) PCT Pub. No.: WO2014/036187
PCT Pub. Date: Mar. 6, 2014

(65) Prior Publication Data
US 2015/0225685 A1    Aug. 13, 2015

Related U.S. Application Data

(60) Provisional application No. 61/694,184, filed on Aug. 28, 2012.

(51) Int. Cl.
*C12P 21/02* (2006.01)
*C12M 3/00* (2006.01)
(Continued)

(52) U.S. Cl.
CPC ............ *C12M 23/44* (2013.01); *C12M 23/00* (2013.01); *C12M 23/42* (2013.01); *C12M 23/52* (2013.01);
(Continued)

(58) Field of Classification Search
CPC ...... C12M 23/00; C12M 23/42; C12M 23/44; C12M 23/52; C12M 25/10; C12M 41/00; C12M 41/14; C12M 41/48
See application file for complete search history.

(56) References Cited

U.S. PATENT DOCUMENTS

| | | |
|---|---|---|
| 3,148,624 A | 9/1964 | Baldwin |
| 4,047,844 A | 9/1977 | Robinson |

(Continued)

FOREIGN PATENT DOCUMENTS

| | | |
|---|---|---|
| EP | 0 164 020 | 8/1989 |
| EP | 1 400 691 | 3/2004 |

(Continued)

OTHER PUBLICATIONS

International Search Report dated Nov. 7, 2007 for International Patent Application No. PCT/US2007/012053, filed May 21, 2007 (2 pp.).

(Continued)

*Primary Examiner* — Michael Hobbs
(74) *Attorney, Agent, or Firm* — Saliwanchik, Lloyd & Eisenschenk

(57) ABSTRACT

The present invention provides a production module for large-scale production of cells and/or cell-derived products such as antibodies or virus; a production suite comprising a plurality of functionally connected production modules of the invention; and a method for large-scale production of cells and/or cell-derived products using the production modules and/or production suites of the invention.

14 Claims, 7 Drawing Sheets

(51) Int. Cl.
*C12M 1/12* (2006.01)
*C12M 1/00* (2006.01)
*C12M 1/34* (2006.01)
*C12M 1/36* (2006.01)

(52) U.S. Cl.
CPC ............ *C12M 25/10* (2013.01); *C12M 41/00* (2013.01); *C12M 41/14* (2013.01); *C12M 41/48* (2013.01); *C12P 21/02* (2013.01)

(56) References Cited

U.S. PATENT DOCUMENTS

| | | |
|---|---|---|
| 4,282,902 A | 8/1981 | Haynes |
| 4,417,861 A | 11/1983 | Tolbert |
| 4,604,038 A | 8/1986 | Belew |
| 4,804,628 A | 2/1989 | Cracauer et al. |
| 4,973,558 A | 11/1990 | Wilson |
| 5,113,906 A | 5/1992 | Högner |
| 5,318,413 A | 6/1994 | Bertoncini |
| 5,330,915 A | 7/1994 | Wilson et al. |
| 5,416,022 A | 5/1995 | Amiot |
| 5,541,105 A | 7/1996 | Melink et al. |
| 5,554,123 A | 9/1996 | Herskowitz |
| 5,571,720 A | 11/1996 | Grandics et al. |
| 5,622,857 A | 4/1997 | Goffe |
| 5,631,006 A | 5/1997 | Melink et al. |
| 5,656,421 A | 8/1997 | Gebhard et al. |
| 5,958,763 A | 9/1999 | Goffe |
| 5,998,184 A | 12/1999 | Shi |
| 6,001,585 A | 12/1999 | Gramer |
| 6,733,252 B2 | 5/2004 | Feygin et al. |
| 7,377,686 B2 | 5/2008 | Hubbard |
| 7,654,982 B2 | 2/2010 | Carlisle et al. |
| 7,935,504 B2 | 5/2011 | Chen |
| 8,133,042 B2 | 3/2012 | Yajima |
| 8,383,397 B2 | 2/2013 | Wojciechowski et al. |
| 8,540,499 B2 | 9/2013 | Page et al. |
| 9,441,195 B2 | 9/2016 | Wojciechowski et al. |
| 9,534,198 B2 | 1/2017 | Page et al. |
| 2003/0040104 A1 | 2/2003 | Barbera-Guillem |
| 2003/0217957 A1 | 11/2003 | Bowman, Jr. et al. |
| 2004/0057856 A1 | 3/2004 | Saxer et al. |
| 2006/0016487 A1 | 1/2006 | Lin |
| 2006/0141623 A1* | 6/2006 | Smith .................... C12M 21/08 435/383 |
| 2006/0257998 A1* | 11/2006 | Klaus .................... C12M 23/04 435/289.1 |
| 2007/0062872 A1 | 3/2007 | Parker et al. |
| 2007/0148010 A1 | 6/2007 | Michels et al. |
| 2007/0292410 A1 | 12/2007 | Cashman et al. |
| 2008/0017194 A1 | 1/2008 | Hassanein et al. |
| 2009/0215022 A1 | 8/2009 | Page et al. |
| 2009/0269841 A1 | 10/2009 | Wojciechowski et al. |
| 2010/0015696 A1 | 1/2010 | Claes et al. |
| 2010/0105138 A1 | 4/2010 | Dodd et al. |
| 2011/0212493 A1 | 9/2011 | Hirschel et al. |
| 2012/0086657 A1 | 4/2012 | Stanton, IV et al. |
| 2012/0114634 A1 | 5/2012 | Stergiou et al. |
| 2013/0058907 A1 | 3/2013 | Wojciechowski et al. |
| 2014/0024012 A1 | 1/2014 | Page et al. |
| 2015/0111252 A1 | 4/2015 | Hirschel et al. |
| 2016/0362650 A1 | 12/2016 | Wojciechowski et al. |
| 2016/0362652 A1 | 12/2016 | Page et al. |

FOREIGN PATENT DOCUMENTS

| | | |
|---|---|---|
| EP | 1 286 696 | 11/2006 |
| WO | WO-2002/087662 | 11/2002 |
| WO | WO-2003/087292 | 10/2003 |
| WO | WO-2005/031167 | 4/2005 |
| WO | WO-2005/087915 | 9/2005 |
| WO | WO-2005/090403 | 9/2005 |
| WO | WO-2005/116186 | 12/2005 |
| WO | WO-2007/136821 | 11/2007 |
| WO | WO-2007/139742 | 12/2007 |
| WO | WO-2007/139746 | 12/2007 |
| WO | WO-2007/139747 | 12/2007 |
| WO | WO-2007/139748 | 12/2007 |
| WO | WO-2010/042644 | 4/2010 |
| WO | WO-2010/048417 | 4/2010 |
| WO | WO-2012/021840 | 2/2012 |
| WO | WO-2012/064760 | 5/2012 |
| WO | WO-2012/171026 | 12/2012 |
| WO | WO-2012/171030 | 12/2012 |
| WO | WO -2013/086418 | 6/2013 |

OTHER PUBLICATIONS

International Search Report dated Oct. 4, 2007 for International Patent Application No. PCT/US2007/012042, filed May 21, 2007 (2 pp.).

International Search Report dated Oct. 4, 2007 for International Patent Application No. PCT/US2007/012052, filed May 21, 2007 (2 pp.).

International Search Report dated Oct. 5, 2007 for International Patent Application No. PCT/US2007/012051, filed May 21, 2007 (2 pp.).

International Search Report dated Sep. 25, 2007 for International Patent Application No. PCT/US2007/012054, filed May 21, 2007 (3 pp.).

Knazek, R. et al., "Cell Culture on Artificial Capillaries: An Approach to Tissue Growth in vitro," *Science*, 1972, vol. 178, No. 4056, pp. 65-67.

Natsume, A. et al., "Engineered Antibodies of IgG1/IgG3 Mixed Isotype with Enhanced Cytotoxic Activities," *Cancer Research*, 2008, vol. 68, No. 10, pp. 3863-3872.

Schubert, S. et al., "Comparison of ceramic hydroxy- and fluoroapatite versus protein A/G-based resins in the isolation of a recombinant human antibody from cell culture supernatant," *J. Chromatography A*, 2007, vol. 1142, pp. 106-113.

Ghaderi, A. et al., "Preparation of anion-exchange resin from styrene-divinylbenzene copolymer obtained by concentrated emulsion polymerization method," *Iranian Polymer Journal*, 2006, vol. 15, pp. 497-504.

\* cited by examiner

BIOMANUFACTURING SUITE AND METHODS FOR LARGE-SCALE PRODUCTION OF CELLS, VIRUSES, AND BIOMOLECULES

CROSS-REFERENCE TO RELATED APPLICATIONS

The present application is the National Stage of International Application No. PCT/US2013/057156, filed Aug. 28, 2013, which claims the benefit of U.S. Provisional Application Ser. No. 61/694,184, filed Aug. 28, 2012, each of which is hereby incorporated by reference herein in its entirety, including any figures, tables, nucleic acid sequences, amino acid sequences, or drawings.

BACKGROUND OF THE INVENTION

The anticipated growth of cell production, virus production, and cell culture-based biomolecule production will require new paradigms for rapid, high-throughput, harvest, purification, concentration and formulation of a variety of cell, viruses, and biomolecules such as proteins and immunoglobulins. Manual methods for producing and purifying these products have their drawbacks. For example, these methods can be labor intensive, time consuming, and are highly inefficient. Large scale manufacturing techniques typically use multiple columns which are manually packed with resin and sterilized prior to each purification run. The manual steps involved in these methods also include a high risk of contamination. Moreover, conventional approaches and tools for these products typically involve numerous manual manipulations that are subject to variations even when conducted by skilled technicians. When used at the scale needed to manufacture hundreds or thousands of different cells, cell lines and patient-specific cell based therapies, for example, the variability, error or contamination rate may become unacceptable for commercial processes.

One type of method for the production of cell-secreted products is to use a bioreactor (e.g., hollow fiber, ceramic matrix, fluidizer bed, etc.) in lieu of the stirred tank. This can bring facilities costs down and increases product concentration. The systems currently available are general purpose in nature and require considerable time from trained operators to setup, load, flush, inoculate, run, harvest, and unload. Each step typically requires manual documentation, which is labor intensive and subject to errors.

Cell culturing devices or cultureware for culturing cells in vitro are known. Hollow fiber perfusion bioreactors (HFBx) were first introduced in 1972 as a model system to study tumors growing at tissue-like densities (R. A. Knazek et al., *Science,* 1972, 178(56):65-67). This system is a high-density, continuous-perfusion system cell culture system that has been used for the production of secreted proteins such as hybridoma, Chinese hamster ovary cells (CHO), human embryonic kidney (HEK) 293 cells, and other mammalian and insect cells. HFBx have been used in a variety of applications such as bioartificial organs, pharmacokinetics, cell therapy, toxicology, etc. In the mid-1980s, Biovest International (formerly Endotronics, Inc.) developed the first commercial scale HFBx system and ever since, the most common application for this technology has been the large-scale production of mammalian cell-secreted proteins, predominantly monoclonal antibodies.

As disclosed in U.S. Pat. No. 4,804,628, the entirety of which is hereby incorporated by reference, a hollow fiber culture device includes a plurality of hollow fiber membranes. Medium containing oxygen, nutrients, and other chemical stimuli is transported through the lumen of the hollow fiber membranes or capillaries and diffuses through the walls thereof into an extracapillary (EC) space between the membranes and the shell of the cartridge containing the hollow fibers. The cells that are to be maintained collect in the EC space. Metabolic wastes are removed from the bioreactor. The cells or cell products can be harvested from the device.

There is a need for a system and method whereby cells and cell-derived products can be produced on a large-scale in an automated, rapid and sterile manner.

BRIEF SUMMARY OF THE INVENTION

An aspect of the invention provides a production module for large-scale production of cells and/or cell-derived products, comprising:
(a) a cultureware module comprising one or more bioreactors (cell growth chambers) and an interface plate (cultureware support structure) with the one or more bioreactors mounted thereto; and
(b) an instrument module comprising hardware to support cell culture growth, wherein the instrument module and the cultureware module are adapted for removable attachment to one another.

In some embodiments, cultureware module includes a plurality of bioreactors. For example, each cultureware module may have 2, 3, 4, 5, 6, 7, 8, 9, 10, 11, 12, or more bioreactors. In some embodiments, the bioreactors are hollow-fiber bioreactors.

Another aspect of the invention concerns production suite comprising a plurality of production modules of the invention, functionally connected. The production suite may further include a room for enclosing the plurality of production modules and having one or more support surfaces for supporting the plurality of production modules. Preferably, the room is environment-controlled (e.g., temperature-controlled) to achieve the desired cell culture conditions. Consequently, no further heat/cooling source is required locally at the site of the bioreactor(s). In some embodiments, the room is a modular and/or relocatable building. For example, the building may have one or more receivers affixed to the building frame or wall, for receiving a lifting attachment allowing transport of the building onto a truck, trailer, vessel, aircraft, or other conveyance.

Another aspect of the invention is a method for large-scale production of cells and/or cell-derived products, comprising providing one or more production modules or one or more production suites of any preceding claim, introducing cells into the one or more bioreactors; culturing the cells to produce grown cells and/or cell-derived products; and harvesting the grown cells and/or cell-derived products. Any desired cell type may be used, e.g., mammalian cells, insect cells, avian cells, or plant cells. Any desired cell-derived product may be produced if a satisfactory cell type(s) is available, such as immunoglobulins, proteins, viruses, and virus-like particles. In one embodiment, the method for large-scale production cells and/or cell-derived products comprises:
providing at least one production module, the production module comprising: (a) a cultureware module comprising one or more bioreactors and an interface plate with the one or more bioreactors mounted thereto, and (b) an instrument module comprising hardware to support cell culture growth, wherein the instrument module and the cultureware module are adapted for removable attachment to one another;

introducing cells into the cell growth chamber;

fluidly attaching a source of cell culture medium to the cultureware module;

operating the pump to circulate the cell culture medium through the bioreactor to grow cells therein; and collecting the grown cells or cell-derived products, and optionally purifying the cells or cell-derived products.

The method may further include removably attaching the production module to the instrument module prior to introduction of the cells. The method may include programming operating parameters into a microprocessor control. In some embodiments, cells are introduced into bioreactors of multiple production modules as a production suite, and grown cells or cell-derived products are collected from the multiple production modules.

BRIEF DESCRIPTION OF THE DRAWINGS

FIG. 5 also shows an online intercapillary metabolic analyzer for sampling fluid and measuring parameters such as lactate and $CO_2$.

DETAILED DESCRIPTION OF THE INVENTION

Figure 1:
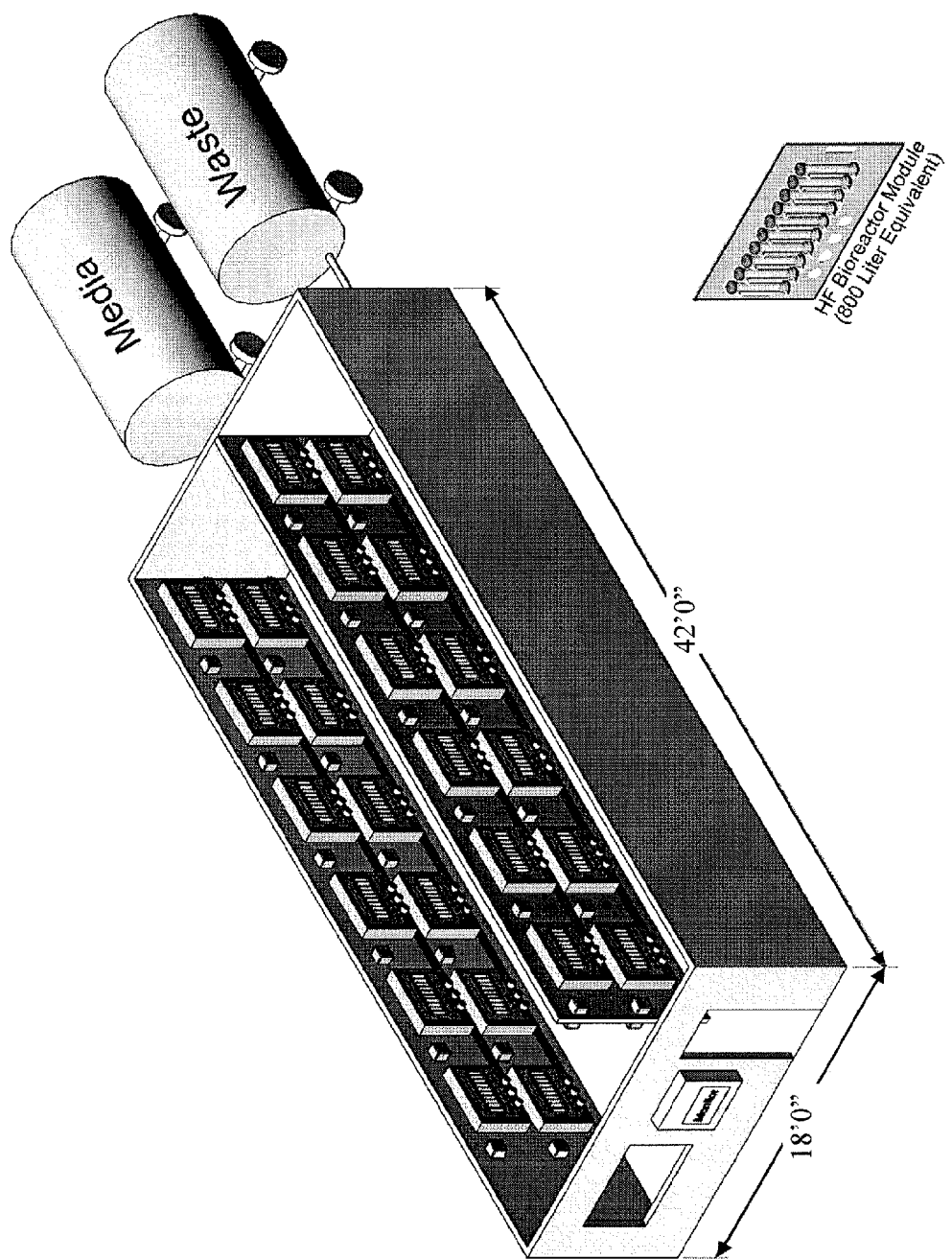
FIG. 1 shows an embodiment of a production suite of the invention, with 48 production modules (a cultureware module having 10 bioreactors installed on the interface plate is shown in the inset).

The present invention concerns a production module, production suite, and method for the large-scale production of cells and cell-derived products, such as proteins, antibodies, virus and virus like particles. The production suite includes multiple instrument modules, preferably situated in a controlled-environment (e.g., temperature, and/or humidity) room. Each instrument module supports a one-time-use disposable cultureware module. The modules have local independent controls to support the cultureware module and are networked to allow coordination between modules or automated analyzers. The modules are repeated to provide a variable large scale production suite. As such, the production suite can start with a small number of instrument modules and be added to as production need increases. The instrument modules can be "hot swapped" so that a module can be removed for maintenance without interfering with the other modules in the suite. The room enclosing the modules is temperature controlled for the culture requirements. The production suite will also have environmental filtration and containment necessary for the product produced. Controlled ingress and egress will be to a gowning area. In order to minimize the number of times the operator needs to gown and enter the room, external control and monitoring stations are provided to allow the operator to check or make adjustments. Video monitoring of the modules may be achieved using video surveillance equipment in the normal visual spectrum, as well as night vision for dark or low light settings.

The cultureware modules will allow ease and quickness of setup with out-of-the-package installation. This will eliminate the need for a biological hood to make aseptic connections. Connection at the cultureware module will be made with sterile fluid connectors or sterile tubing splicer. Fluid sensing elements will come sterile in the cultureware module. Mechanical interfacing will occur when the cultureware module is inserted into the instrument module. Predefined automated procedures will fluidically prepare the cultureware module. Since a variety of different cell and viral types are anticipated, flexibility of inoculation is important. Support for bag, spinner or inter-cultureware module inoculations will be supported. This will allow suspension, attachment dependent or primary cells (such as stem cells) to be used as well as various viral (free virus, infected cells, etc.) infectious agents. The figures show hollow-fiber bioreactors being used to support the culture but other bioreactors (such as synthetic or biological based scaffolding, immobilization gel, etc.) may be used depending on the culture requirements. Harvesting of product (such as expressed protein, viruses, viral particles, or cells) is equally important. Harvest can be from an individual cultureware module to a container, a group of modules to a container (batch harvest), or use of the harvest (individual or batch) to inoculated other cultureware modules. Online monitoring of the cultureware module will be done at the instrument module using the pre-sterile sensing elements (such as pH or dissolved oxygen) or instrument module sensors (such as gas pressure, mass flow, fluid flow or off-gas $CO_2$). The cultureware module will support offline analysis for sensor calibration, metabolic analysis and cell/product analysis.

One aspect of the invention provides a production module for large-scale production of cells and/or cell-derived products, comprising:

(a) a cultureware module comprising one or more bioreactors (cell growth chambers) and an interface plate (cultureware support structure) with the one or more bioreactors mounted thereto; and (b) an instrument module comprising hardware to support cell culture growth, wherein the instrument module and the cultureware module are adapted for removable attachment to one another.

In some embodiments, cultureware module includes a plurality of bioreactors. For example, each cultureware module may have 2, 3, 4, 5, 6, 7, 8, 9, 10, 11, 12, or more bioreactors. In some embodiments, the bioreactors are hollow-fiber bioreactors.

Another aspect of the invention concerns production suite comprising a plurality of production modules of the invention, functionally connected. The production suite may further include a room for enclosing the plurality of production modules and having one or more support surfaces for supporting the plurality of production modules. Preferably, the room is environment-controlled (e.g., temperature-controlled) to achieve the desired cell culture conditions. Consequently, no further heat/cooling source is required locally at the site of the bioreactor(s). In some embodiments, the room is a modular and/or relocatable building. For example, the building may have one or more receivers affixed to the building frame or wall, for receiving a lifting attachment allowing transport of the building onto a truck, trailer, vessel, aircraft, or other conveyance.

Another aspect of the invention is a method for large-scale production of cells and/or cell-derived products, comprising providing one or more production modules or one or more production suites of any preceding claim, introducing cells into the one or more bioreactors; culturing the cells to produce grown cells and/or cell-derived products; and harvesting the grown cells and/or cell-derived products. Any desired cell type may be used, e.g., mammalian cells, insect cells, avian cells, or plant cells. Any desired cell-derived product may be produced if a satisfactory cell type(s) is available, such as immunoglobulins, proteins, viruses, and virus-like particles. In one embodiment, the method for large-scale production cells and/or cell-derived products comprises:

providing at least one production module, the production module comprising: (a) a cultureware module comprising one or more bioreactors and an interface plate with the one or more bioreactors mounted thereto, and (b) an instrument module comprising hardware to support cell culture growth, wherein the instrument module and the cultureware module are adapted for removable attachment to one another;

introducing cells into the cell growth chamber;

fluidly attaching a source of cell culture medium to the cultureware module;

operating the pump to circulate the cell culture medium through the bioreactor to grow cells therein; and collecting the grown cells or cell-derived products, and optionally purifying the cells or cell-derived products.

The method may further include removably attaching the production module to the instrument module prior to introduction of the cells. The method may include programming operating parameters into a microprocessor control. In some embodiments, cells are introduced into bioreactors of multiple production modules as a production suite, and grown cells or cell-derived products are collected from the multiple production modules.

Some examples of applications for which the production modules, production suites, and methods of the present invention include, but are not limited to:

The production of monoclonal antibodies from hybridoma cell lines (e.g., the K6H6/B5 or 1D12 hybridoma cell lines).

The expansion of autologous patient-derived blood cells including immune cells for therapeutic application.

The expansion of patient derived somatic cells for subsequent re-infusion back into patients for therapeutic purposes. A specific example already available for therapeutic application in patients is the harvesting and expansion of patient-specific cartilage cells (chondrocytes) followed by re-infusion of those cells back into a region containing damaged articular cartilage.

The expansion of patient-derived or generic multipotent cells, including embryonic stem cells, adult stem cells, hematopoeitic stem or progenitor cells, multi- or pluripotent cells derived from cord blood or other sources for therapeutic purposes.

The expansion of somatic or germline cells as in the aforementioned cellular applications and in which the cells have been genetically modified to express cellular components or to confer on them other beneficial properties such as receptors, altered growth characteristics or genetic features, followed by introduction of the cells into a patient for therapeutic benefit. An example is the expansion of patient specific fibroblasts genetically modified to express growth factors, clotting factors, or other biologically active agents to correct inherited or acquired deficiencies of such factors.

The production of virus (such as influenza), VLPs, and viral vectors, e.g., for production of vaccines.

The production of other cell-derived products such as growth factors.

I. PRODUCTION MODULES

Accordingly, an aspect of the invention provides a production module for large-scale production of cells and/or cell-derived products, comprising:

(a) a cultureware module comprising one or more bioreactors (cell growth chambers) and an interface plate with the one or more bioreactors mounted thereto; and (b) an instrument module comprising hardware to support cell culture growth, wherein the instrument module and the cultureware module are adapted for removable attachment to one another.

In some embodiments, cultureware module includes a plurality of bioreactors. For example, each cultureware module may have 2, 3, 4, 5, 6, 7, 8, 9, 10, 11, 12, or more bioreactors. In some embodiments, the bioreactors are hollow-fiber bioreactors. In embodiments in which the cultureware module has a plurality of bioreactors, the bioreactors may be arranged in any orientation that permits production of the cells and/or cell-derived products. For example, bioreactors may be arranged in a line in parallel-fashion, as shown in the figures, but other orientations are possible. In some embodiments, the flow path connecting the bioreactors permits a first bioreactor to be inoculated (e.g., with cells and/or virus), resulting in inoculation of "downstream bioreactors" of the production module.

The production module includes two individual parts: a reusable instrument module, and at least one disposable cell cultureware module that is used for a single production run and is disposable. The instrument module provides the hardware to support cell culture growth and production in a compact package, which is advantageous in a facility handling a large number of unique cell lines, for example. A pump, such as an easy-load 4 channel peristaltic pump, moves fresh basal media into the cultureware, removes spent media, adds high molecular weight factor and removes product harvest. A temperature controlled storage area can be used to maintain the factor and harvest at a low temperature (preferably, approximately 4° C.). A heating mechanism can maintain the cell environment to promote growth and production. The gas blending mechanism, in conjunction with the cultureware pH sensor controls the pH of the cell culture medium. A plurality of automated tube valving drives (e.g., two automated tube valving drives) are used to control the cultureware flow path configuration to accomplish the fluidic functions necessary to initiate and carryout a successful run. Valves and sensors in the instrumentation base device control the fluid cycling in the cultureware. Drive for fluid circulation is provided. An identification code reader (such as a barcode reader, radio frequency identification (RFID) tag reader, bokode reader, or quick response (QR) code reader) is preferably included to facilitate operator and lot tracing. A communication port preferably ties the instrument module to a facilities data management system (LIMS). The instrument module of the production module can include a user interface, such as a flat panel display with touch screen, for user interaction. Likewise, an interface can be provided for interacting with a production suite made up of a plurality of production modules.

The one-time use cultureware is provided pre-sterilized, designed for rapid loading onto the instrument module ("quick-load"; see, for example, WO 2007/139742 (Wojciechowski et al., "Method and System for the Production of Cells and Cell Products and Applications Thereof", published Dec. 6, 2007, which is incorporated herein by reference in its entirety). The loading of the cultureware module makes connections to the instrument module through the interface plate. Optionally, a pump cassette, which is physically attached to the tubing, can allow the user to quickly load the pump segments. The design and layout minimizes loading errors. The cultureware enclosure provides an area that may be heated to maintain cell fluid temperature. Reservoirs to maintain fluid volumes and cycling are included in the cultureware. Sensors for fluid circulation rate and pH and thermal well for the instrument module's temperature sensor are included. The blended gas from the instrument module is routed to the gas exchange cartridge that provides oxygen and adds or removes carbon dioxide to the circulated fluid to support cell metabolism. The cultureware module also includes a bioreactor (e.g., hollow fiber bioreactor or other bioreactor type), which provides the cell space and media component exchange. Disposable containers for harvest collection and flushing can be utilized. The operator attaches a media source, factor source, and spent media container to the cultureware before running. The media and spent media container is disconnected, pump cassette is unloaded, cultureware body is unloaded and the used cultureware can be placed in a biohazard container for disposal.

The present invention provides a large-scale production module for producing cells and cell derived products in a closed, self-sufficient environment. More specifically, the production module allows for large-scale cell expansion and harvest of cells and their products with minimal need for technician interaction.

As will be described further herein, the device incorporates cell culture technology, for example, hollow fiber or similar bioreactor perfusion technology, with all tubing components, harvest tubing and tubes threaded through a pump cassette, encased in a disposable bioreactor. Following bioreactor inoculation with cells, the production module follows pre-programmed processes to deliver media, maintain pH, maintain lactate levels, control temperature and harvest cells or cell-secreted protein. Standard or unique cell culture growth parameters can be programmed such that various cell types can be expanded and such that virus or VLP can be harvested in an efficient, reproducible manner with minimal chance of human error.

The production module is based on cell growth chamber technology. For example, bioreactors that have a plurality of semi-permeable hollow fibers or other type of semi-permeable membrane or substrate potted (attached) in a housing to create a space inside the fiber or one side of the membrane (referred to as intracapillary (IC) space) separate from that outside the fibers or on the other side of the membrane (referred to as extracapillary (EC) space). Fluid distribution between the IC space and EC space occurs through the fiber pores which can range in size based on the application. Cells are placed on one side of the fiber or membrane, usually in the EC space, in a complete cell culture medium, which is usually the same medium used to expand cells prior to bioreactor inoculation (serum containing, serum-free, or protein-free medium). Cells are usually placed in the EC space when secreted protein is the desired product. In some instances, when cells are the desired product, it may be beneficial to place cells in the IC space.

Medium is perfused through a bioreactor by circulating through the IC space at a fast rate. The medium can be a liquid containing a well-defined mixture of salts, amino acids, and vitamins that often contain one or more protein growth factors. This serves to deliver nutrients to the cell space and conversely, removes or prevents a toxic build-up of metabolic waste. During this circulation, medium is passed through an oxygenator or gas exchanger cartridge 24 which serves to provide pH control and oxygen for the cells and conversely, remove carbon dioxide from the culture. When the bioreactor contains a smaller number of cells, just after inoculation, the oxygenator or gas exchange cartridge is used to provide $CO_2$ and subsequently control pH of the culture environment. As cell number increases, the oxygenator is used to remove $CO_2$ which serves to enhance acid neutralization and control the pH of the culture. Other bioreactor configurations, in addition to hollow fibers, that are designed and optimized for the growth and production of cells and production of cell-derived products may also be used.

The production module provides significant efficiencies and cost reduction through its disposable component and enclosed operation. As such, cell lines are contained in a closed system and continuously cultured without the need for specialized, segregated clean rooms. This fully integrated apparatus eliminates the need for cleaning and sterilization validations, as well as the need for hard plumbing associated with conventional cell culture facilities.

The production module includes two individual parts: an instrument module that is reusable and an enclosed cultureware module that may be used for a single production run and is disposable. Numerous production modules can be used as a production suite. The instrument provides the hardware to support cell culture growth and production in a compact package.

An easy-load multiple channel peristaltic pump drive (see WO 2007/139742, incorporated by reference) can be located in the instrument module and a pump cassette can move fresh basal media into the cultureware, removes spent media, adds growth factors or other supplements and removes product harvest. A gas exchange cartridge in conjunction with a cultureware pH sensor can be included to control the pH of the cell culture medium. Automated tube valving drives can be used to control the cultureware flow path configuration to accomplish the fluidic switching functions needed to initiate and do a successful run. Valves and sensors can be used to control fluid cycling in the cultureware module (see WO 2007/139748 (Page et al., "Extra-Capillary Fluid Cycling System and Method for a Cell Culture Device", published Dec. 6, 2007, which is incorporated herein by reference in its entirety). A pump drive for fluid circulation is provided. A wireless or tethered (attached) identification code reader (such as a barcode reader, radio frequency identification (RFID) tag reader, or quick response (QR) code reader) may be used by an operator to facilitate lot tracing. An identification code comprises an identifier on or made part of a surface such as cultureware module or user identification tag, and which may include, but is not limited to, a bar code, a radio frequency identification tag, a number, a series of numbers, a color, a series of colors, a letter, a series of letters, a symbol, a series of symbols, and a combination of one or more of the foregoing. A communication port ties the instrument to a data information management system (such as a MES). A user interface, such as a keyboard and/or flat panel display with touch screen capability is available for user interaction.

The cultureware module of the production module is provided pre-sterilized. It is designed for quick loading onto the instrument module ("quick-load"), as described in WO 2007/139742 and WO 2007/139747 (Page et al., "Interface of a Cultureware Module in a Cell Culture System and Installation Method", published Dec. 6, 2007, which is incorporated herein by reference in its entirety). The loading of the cultureware module makes connections to the instrument. A pump cassette can be physically attached to the tubing, allowing the user to quickly load the pump segments. This design and layout minimizes loading errors.

The cultureware enclosure provides an area that can be heated internally or by external devices to maintain cell fluid temperature. A fluid cycling unit can be used (see WO 2007/139748, which is incorporated herein by reference in its entirety) to maintain fluid volumes and cycling and can be included in the production module. Sensors for fluid circulation rate, pH and a thermal well for the instrument's temperature sensor are provided. The blended gas from the instrument module is routed to gas exchange cartridge that provides oxygen and adds or removes carbon dioxide to the circulated fluid to support cell metabolism. A magnetically coupled pump drive can be used to circulate fluid thru the bioreactor(s) and gas exchange cartridge (see, for example, WO 2007/139742, which is incorporated by reference in its entirety). The bioreactor that provides the cell space and media component exchange is also in the cultureware.

Cell expansion and subsequent process tracking can be facilitated by generation of a batch record for each culture. Historically, this is done with a paper-based system that relies on operator input of the information. This is labor intensive and subject to errors. The production module and production suite of the invention can incorporate an identification code reader (such as a barcode reader, radio frequency identification (RFID) tag reader, bokode reader, or quick response (QR) code reader), and data gathering software which, when used with the information management system (MES), allows for automatic generation of the batch record.

The production module and production suite of the present invention has application in a regulated cell culture environment. It is anticipated that the production of viral vaccines may require the simultaneous culture of numerous cell lines in a single facility. In addition to the segregation created through this closed culture approach, the production module and production suite is designed to support a standard information management system (such as a LIMS or MES) protocol. This capability contributes to the creation of thorough batch records and verification of culture conditions to ensure standardization, tracking and safety of each product. This capability facilitates the multi-product concept that is pivotal to facilities involved with infectious products.

As described above, module 12 is heated to maintain cell fluid temperature. Heating mechanism 22 (FIG. 6) maintains the cell environment to promote growth and production.

Figure 2:
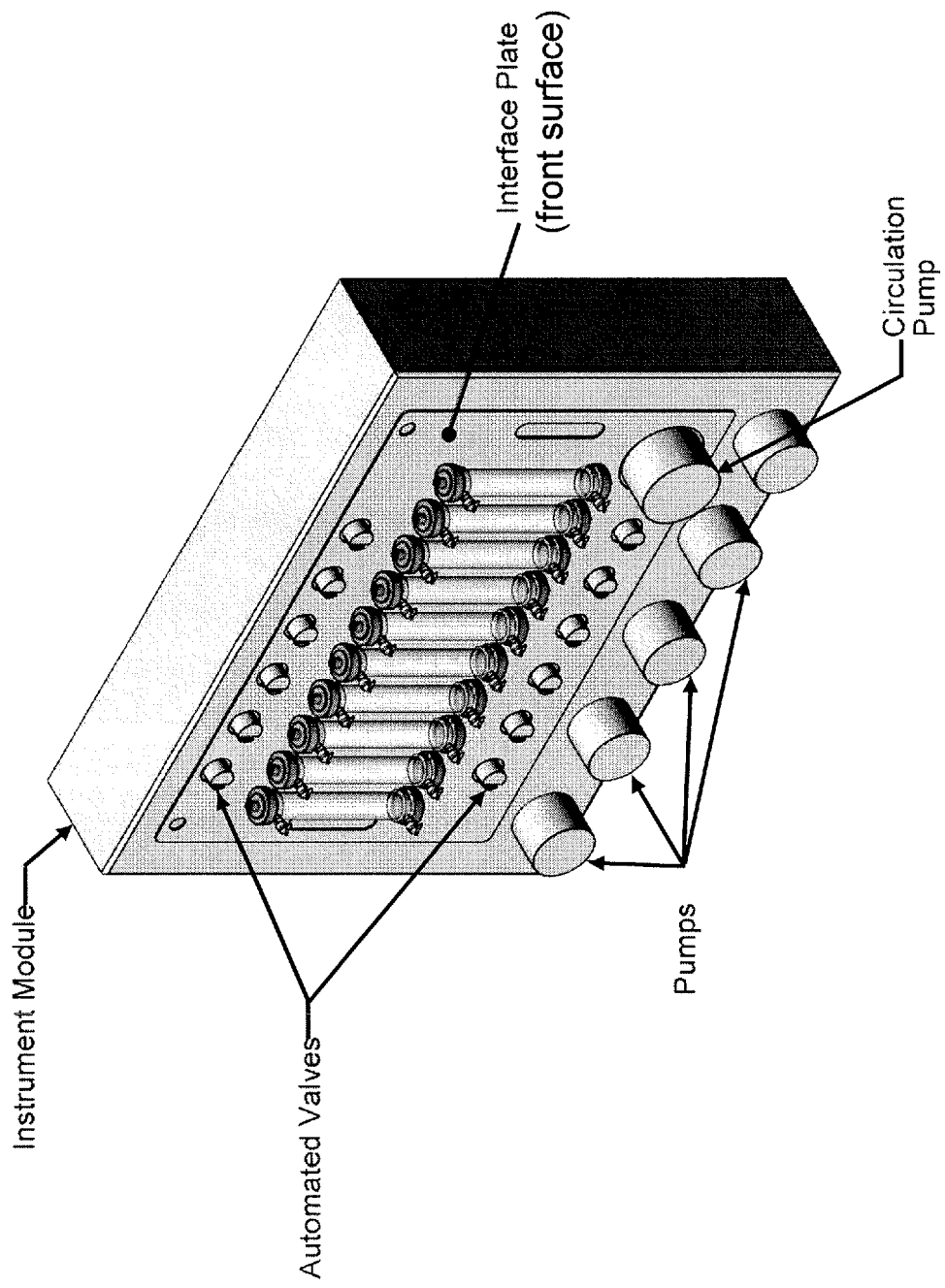
FIG. 2 shows an embodiment of a production module of the invention, including an instrument module and a cultureware module including the front surface of an interface plate and a series of bioreactors between the automated valves.
Figure 6:
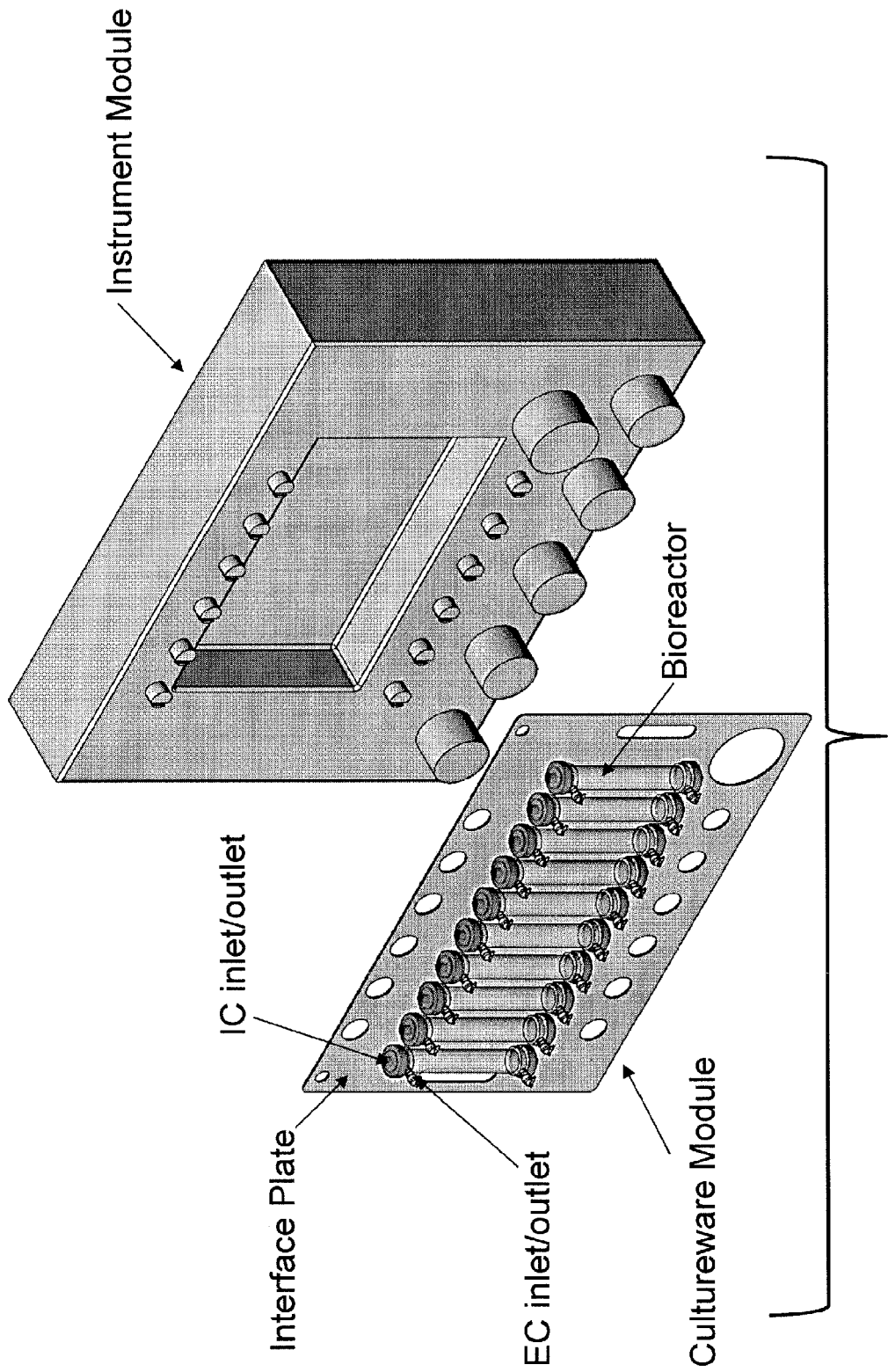
FIG. 6 shows an embodiment of a cultureware module and instrument module of the invention. Together, the cultureware module and instrument module are referred to as a production module.
Figure 7:
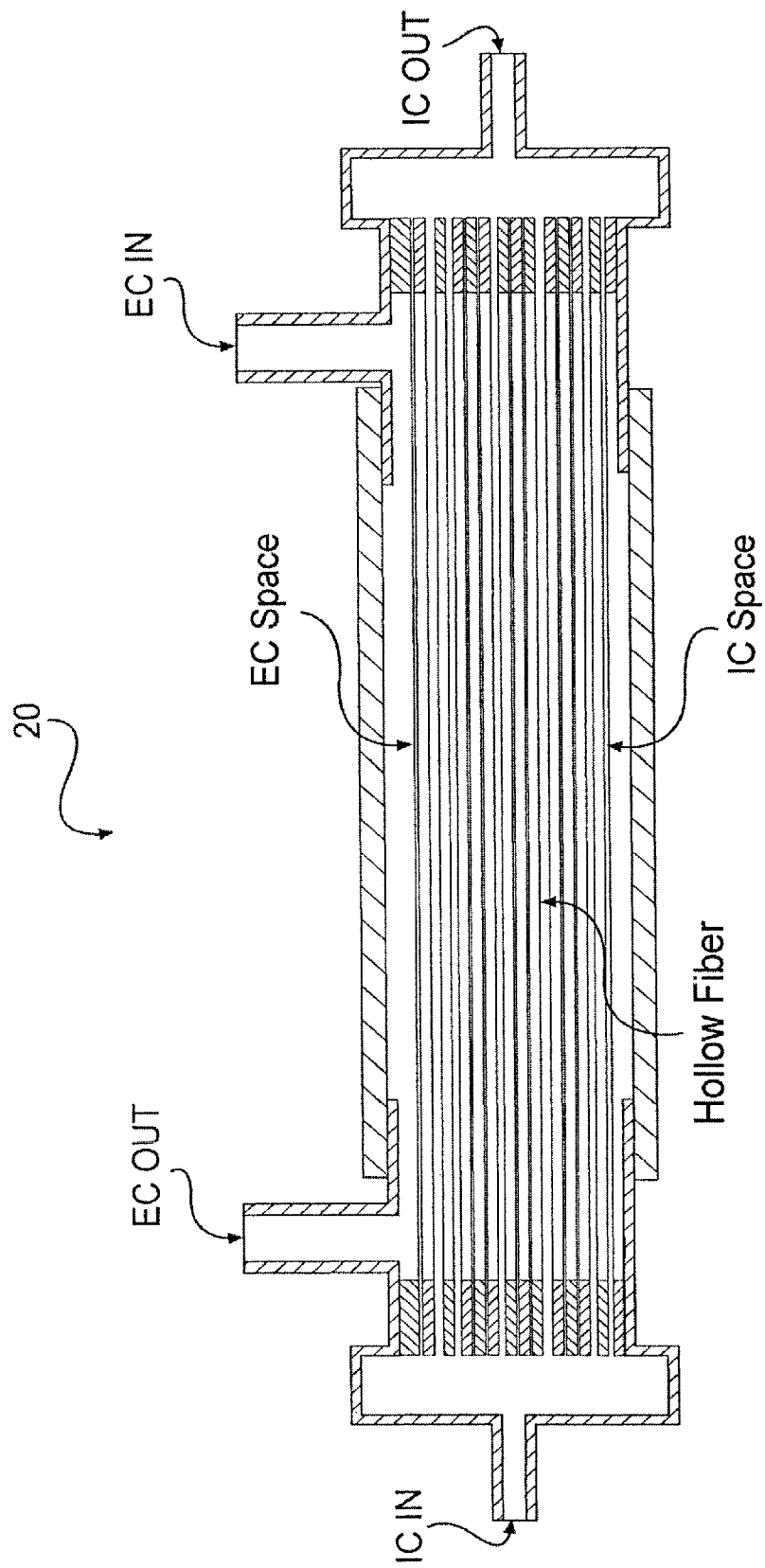
FIG. 7 shows an embodiment of a hollow fiber perfusion bioreactor which may be used in the production modules, production suites, and methods of the invention, with hollow fibers and in and out ports for the intracapillary space and extracapillary space indicated. As will be appreciated by those skilled in the art, the sidedness and orientation of the ports on the bioreactor are not critical.

During installation, the cultureware module is aligned with the connections of the instrument module and the cultureware module is placed into the operating position as shown in FIGS. 2 and 6. All mating interface features are functional. The cultureware module can be inserted into the instrument in an operating position with no special operator procedures required for loading the tubing into the clamps. It provides automated actuation of slide clamp, compactness, multiple lines, maintains clamp position even with loss of actuator power, less costly than an equivalent switching valve. Offset occluded/open position of two tubing lines can insure a make-before-break switching of fluids. No power is required to maintain any operating position.

In one embodiment, the bioreactor is a flexible bioreactor having a flexible outer body that allows for physical movement of the cell growth substratum (hollow fibers, membrane or other suitable matrix) when a resultant torquing or bending moment is applied to the bioreactor ends. A flexible outer body allows for the bioreactor case to be flexed, causing fiber movement. This fiber movement enhances the release of cells that have attached to the side of the bioreactor matrix, if harvesting of cells is desired. The cells can then be harvested by flushing either after or during the manipulation. This method can provide increased efficiency of cell harvest at high cell viabilities without the use of chemical or enzymatic release additives. Alternatively, the bioreactor can have a rigid outer body.

Optionally, a bioreactor can be constructed using an outer housing that incorporates a flexible center section. This center section can be composed of a flexible, non-permeable tubing that allows each end of the bioreactor to be manipulated, thus causing movement of the growth matrix. The purpose of this movement is to release the attachment or clumping of products on the extra-capillary (EC) side of the fibers. The products can then be flushed from the EC via the access port at each end of the bioreactor.

Harvesting cells from a matrix-containing bioreactor such as a hollow fiber bioreactor has been difficult to accomplish. Typically, cells are sticky and attach themselves to the fibers or to other cells and form clusters. Rapid flushing of media through the EC space to hydraulically force the cells free and into the harvest stream is the most basic method of harvesting cells from the EC space. Typically the quantity of cells harvested is low because the flushing media tends to shunt through the EC and flush cells only from the limited fluid path.

Another method is to physically shake or impact the outer housing to release the cells or clumps of cells. This practice may cause physical damage to the bioreactor or its associated components. Another method includes the use of chemicals to disrupt the adhesion of cells to the fibers or to disrupt the clumps of cells. Adding chemicals to a controlled process may cause adverse effects on cell viability and can introduce an unwanted agent in the down-stream processing.

The production module and production suite of the invention fully integrates the concept of disposable cultureware into automated process control for maintaining and expanding specialized cells (primary cells or cell lines) for a duration of any time needed. To accomplish this, the apparatus of the present invention was designed for EC space fluid flow that enhances cell growth in high density perfusion culture, yet remains completely closed and disposable.

The integrated pre-assembled cultureware, which includes all tubing, bioreactor, oxygenator, and pH probe, is enclosed in a single unit that easily snaps into the apparatus. In addition to this error-proof, quick-load design, the entire cultureware unit enclosed by the casing becomes the cell culture incubator with temperature control regulated through automated process control of the instrument. Pumps and fluid control valves facilitate disposability and error-proof installation, eliminating the possibility of technician mistakes. Finally, during the course of any culture, the closed system can have restricted access except for trained and authorized personnel. For example, manipulations or sampling, outside of program parameters, can require password and identification code (e.g., bar code) access before they can be implemented.

II. PRODUCTION SUITE

Another aspect of the invention concerns a production suite comprising a plurality of production modules of the invention, functionally connected. In some embodiments, the flow path connecting the plurality of production modules permits a first production module to be inoculated (e.g., with cells and/or virus), resulting in inoculation of "downstream production modules". Virtually any number of production molecules per production suite is possible.

The production suite may further include a room for enclosing the plurality of production modules and having one or more support surfaces for supporting the plurality of production modules. Preferably, the room is environment-controlled (e.g., temperature-controlled) to achieve the desired cell culture conditions. Consequently, no further heat/cooling source is required locally at the site of the bioreactor(s). In some embodiments, the room is a modular and/or relocatable building. For example, the building may have one or more receivers affixed to the building frame or wall, for receiving a lifting attachment allowing transport of the building onto a truck, trailer, vessel, aircraft, or other conveyance. The building may include one or more anchors for anchoring the building to the ground.

Another aspect of the invention is a method for large-scale production of cells and/or cell-derived products, comprising providing one or more production modules or one or more production suites of any preceding claim, introducing cells into the one or more bioreactors; culturing the cells to produce grown cells and/or cell-derived products; and harvesting the grown cells and/or cell-derived products. Any desired cell type may be used, e.g., mammalian cells, insect cells, avian cells, or plant cells. Any desired cell-derived product may be produced if a satisfactory cell type(s) is available, such as immunoglobulins, proteins, viruses, and virus-like particles.

Figure 3:
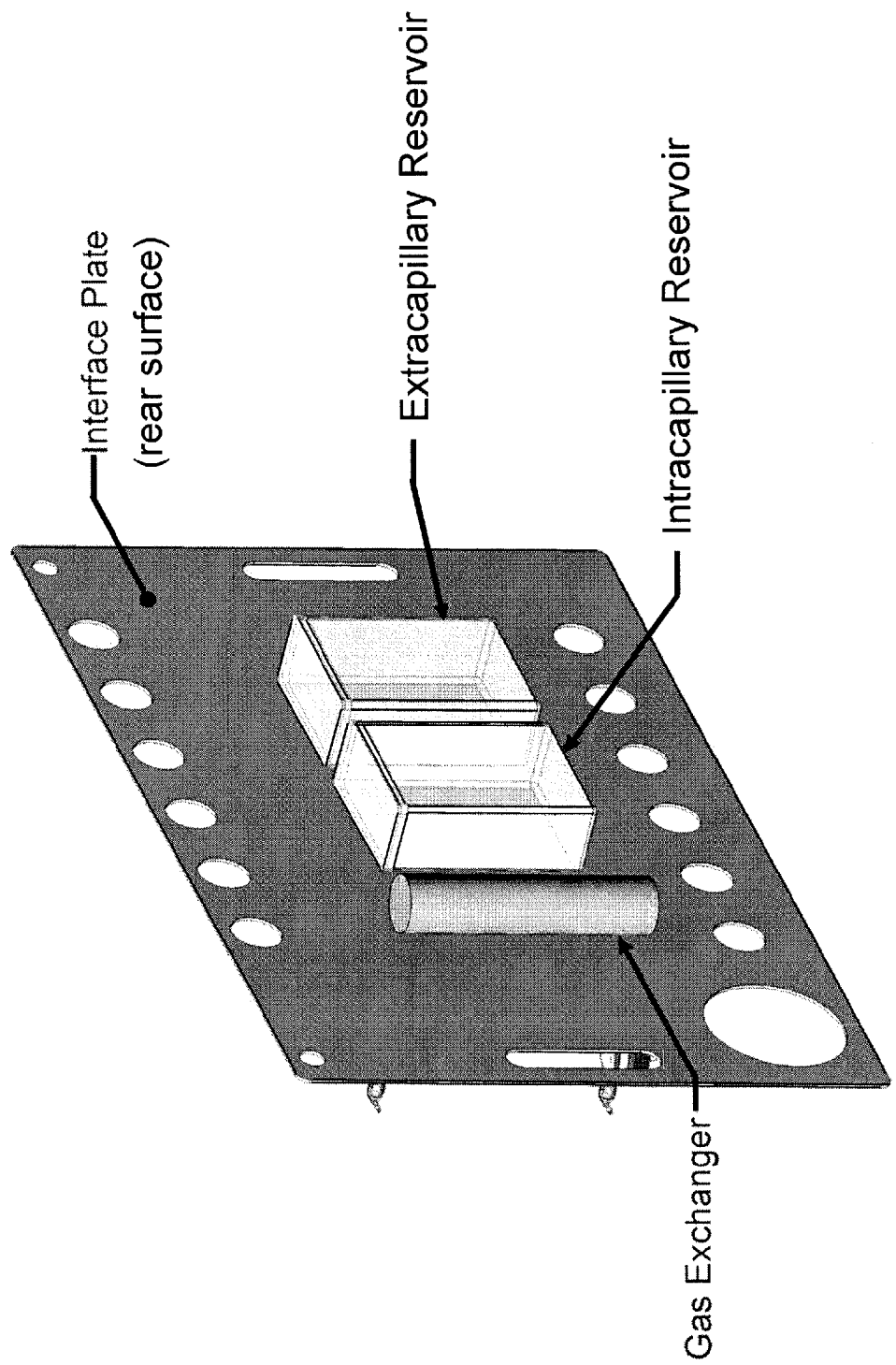
FIG. 3 shows an embodiment of a cultureware module of the invention, showing the rear surface of the interface plate; extracapillary (EC) reservoir and intracapillary (IC) reservoir, which connect to appropriate manifolds for the bioreactor(s) as exemplified in the flow path schematic of FIG. 5; and a gas exchanger connected to one or more bioreactors and the IC reservoir.

Medium is perfused through one or more of the bioreactors of the cultureware module. The medium can be a liquid containing a well-defined mixture of salts, amino acids, and vitamins that often contain one or more protein growth factors. This serves to deliver nutrients to the cell space and conversely, removes or prevents a toxic build-up of metabolic waste. During this circulation, medium is passed through an oxygenator or gas exchanger cartridge (FIGS. 3 and 5) which serves to provide pH control and oxygen for the cells and conversely, remove carbon dioxide from the culture. When the bioreactor contains a smaller number of cells, just after inoculation, the oxygenator or gas exchange cartridge can be used to provide $CO_2$ and subsequently control pH of the culture environment. As cell number increases, the oxygenator is used to remove $CO_2$ which serves to enhance acid neutralization and control the pH of the culture.

Figure 4:
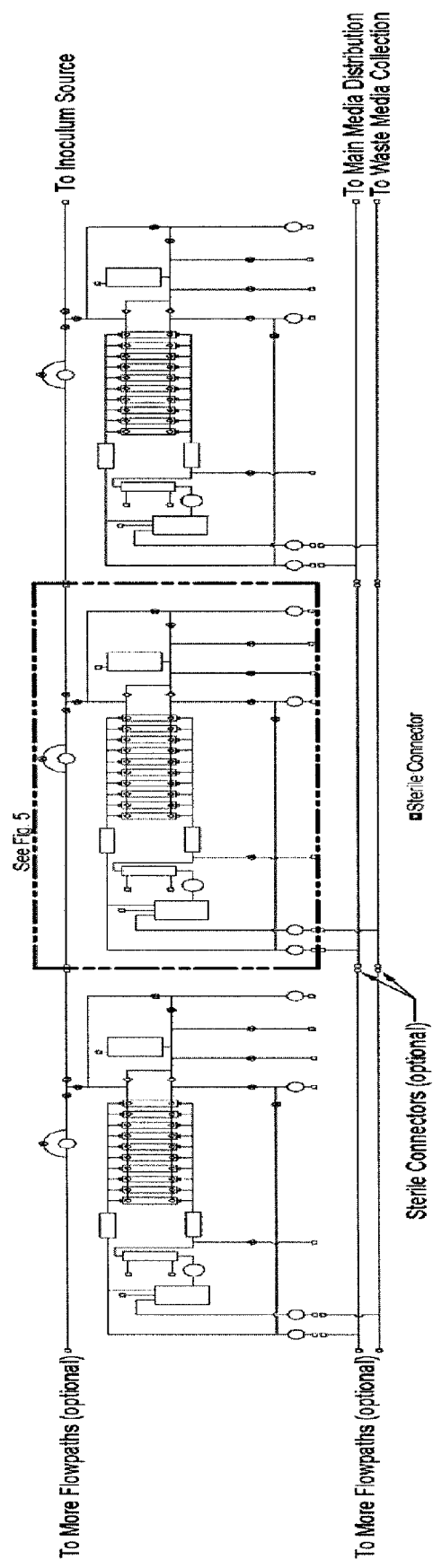
FIG. 4 shows an example of a cultureware flow paths schematic of the invention showing connections between production modules (inter-module connections).
Figure 5:
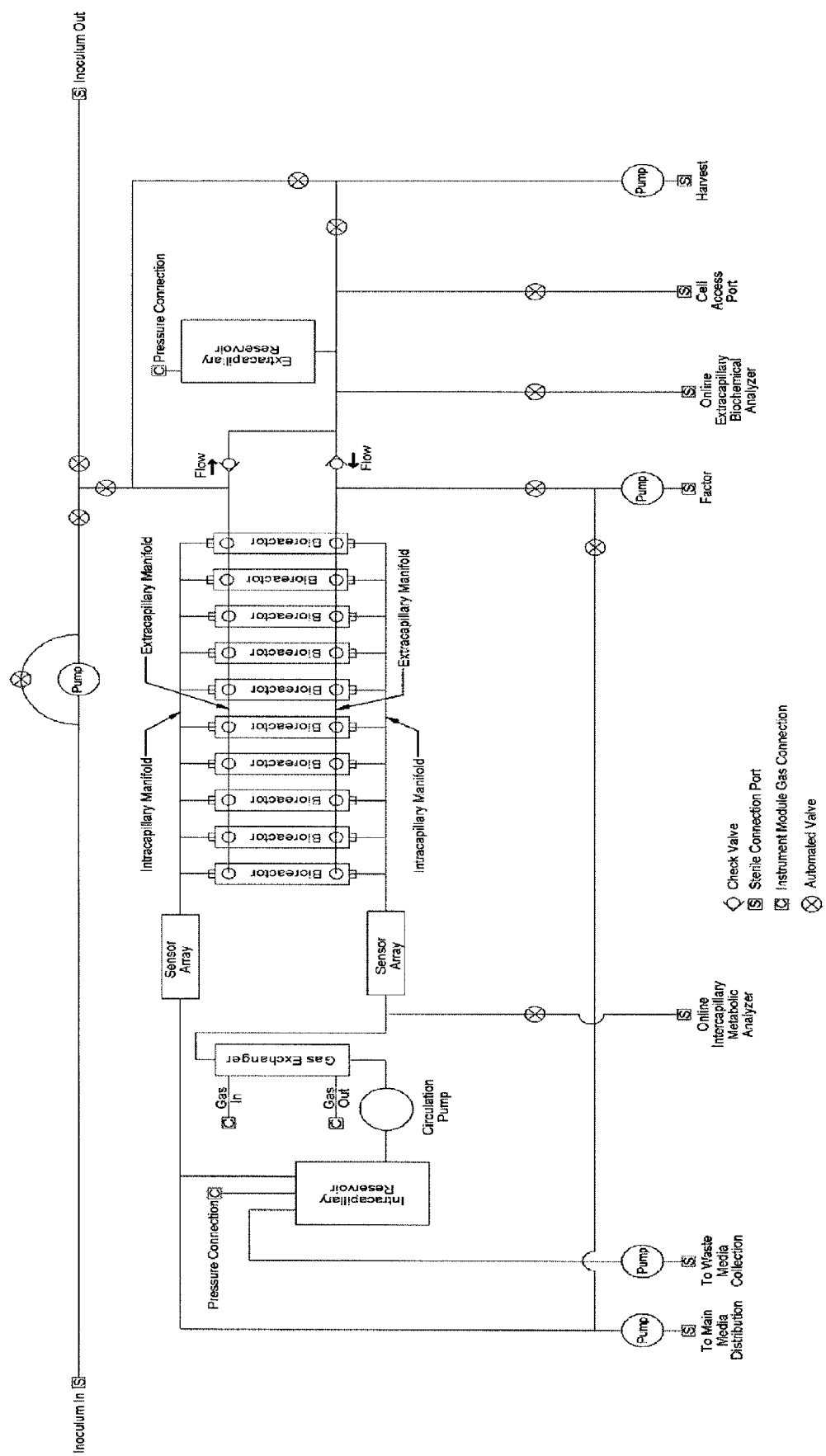
FIG. 5 shows an example of a cultureware module flow path schematic of the invention. Inoculum such as cells and viruses can be introduced as indicated. The schematic includes a pre-bioreactor sensor array (lower sensor array in figure) and post-bioreactor sensor array (upper sensor array in figure), for sensing one or more parameters such as pH, dissolved oxygen, temperature, pressure, and, optionally, various metabolites.

The following is an example of a cell culture run. An operator removes the sterile cultureware from its packaging and mounts it to the instrument module. Mechanical interfacing occurs automatically when the cultureware is inserted. Cultureware module information is scanned by the instrument and stored for the batch record. Sterile connections are made to the media source, waste factor and harvest (FIG. 5) vessels. The operator starts the process and the instrument automatically sequences through the process of flushing and preparing the cultureware module for inoculation. Throughout the run, online intercapillary metabolic analysis (FIG. 5) can be used to verify the sensor array and provide additional information to the instrument. Just before inoculation, factor supplemented media is introduced into the extracapillary space. Once prepared, the desired cells can be introduced locally through the Inoculum-In (pumped into the bioreactors) or diverted from neighboring cultureware modules (FIGS. 4 and 5). The instrument sequence shifts into a growth mode to expand the cell mass. Medium is perfused through the bioreactors of the cultureware module. This serves to deliver nutrients to the cell space and conversely, removes or prevents a toxic build-up of metabolic waste. During this circulation, medium is passed through an oxygenator or gas exchanger cartridge (FIGS. 3 and 5) which serves to provide pH control and oxygen for the cells and conversely, remove carbon dioxide from the culture. When the bioreactor contains a smaller number of cells (e.g., immediately after inoculation), the oxygenator or gas exchange cartridge can be used to provide $CO_2$ and subsequently control pH of the culture environment using the sensors built into the cultureware module (FIG. 5). As cell number increases, the oxygenator is used to remove $CO_2$ which serves to enhance acid neutralization and control the pH of the culture. The online extracapillary biochemical analysis (FIG. 5) provides information concerning the product concentration or cell mass. In the case of virus production, when the cell mass is determined to be optimal (for example, after a number of days), the operator will initiate introduction of virus and/or virus-infected cells (e.g., Influenza virus and/or Influenza infected cells) into the cell mass locally through the Inoculum-In (pumped into the bioreactors) or diverted from neighboring infected cultureware modules (FIGS. 4 and 5). After an infection period, harvesting of the infectious (plaque-forming) virus is started, which can be locally from the harvest line or network-wide from the Inoculum-Out line. Alternatively, if the product is not a virus (e.g., cells or biomolecules such as antibodies or other polypeptides), agents such as cytokines can be introduced to the cells to induce a desired response or production of a desired product. When a significant drop in one or more metabolics is observed, harvesting is stopped. The operator removes the harvest, if local, and indicates the run is complete. The instrument module prepares for cultureware removal. Sterile disconnects are made for the inoculum, media and waste lines. The cultureware module is removed and preferably disposed of as a biological hazard. The instrument module surfaces can be spray cleaned. The instrument is then ready for the next production run.

A wide variety of media, salts, media supplements, and products for media formulation can be utilized to produce the cells and cell-derived products, depending upon the particular cell type or types. Examples of these substances include, but are not limited to, carrier and transport proteins (e.g., albumin), biological detergents (e.g., to protect cells from shear forces and mechanical injury), biological buffers, growth factors, hormones, hydrosylates, lipids (e.g., cholesterol), lipid carriers, essential and non-essential amino acids, vitamins, sera (e.g., bovine, equine, human, chicken, goat, porcine, rabbit, sheep), serum replacements, antibiotics, antimycotics, and attachment factors. These substances can be present in various classic and/or commercially available media, which can also be utilized with the subject invention. Examples of such media include, but are not limited to, Ames' Medium, Basal Medium Eagle (BME), Click's Medium, Dulbecco's Modified Eagle's Medium (DMEM), DMEM/Nutrient Mixture F12 Ham, Fischer's Medium, Minimum Essential Medium Eagle (MEM), Nutrient Mixtures (Ham's), Waymouth Medium, and William's Medium E.

The cell culture environment within each bioreactor can be manipulated individually, or as a group, by exposing the cells to agents/techniques (e.g., cytokines, hormones, feed strategies, temperatures, growth or cell cycle inhibitors, co-cultures) to evoke a desirable response from the process. This can, for example, enhance productivity, shorten process times and/or produce secondary effects or products. One or more of such agents can be included as a component of media or added to the culture environment. For example, stem cells can be exposed to agents to induce or inhibit differentiation, and lymphocytes can be exposed to specific antigens to produce a T-cell response.

III. CELL PRODUCTION

The subject invention provides a ready source of cells for medicine and research, including pharmacological studies for the screening of various agents, and toxicologic studies for the cosmetic and pharmaceutical industries. Any cells desired for cell production, or any cells useful for production of the cell-derived product of interest can be used in the production module, production suite, and methods of the invention. For example, cells may be human or non-human mammalian cells, insect cells, avian cells, or plant cells. The cells may be transformed or non-transformed cell lines, primary cells including somatic cells such as lymphocytes or other immune cells, chondrocytes, myocytes or myoblasts, epithelial cells and patient specific cells, primary or otherwise. Included also are cells or cell lines that have been genetically modified, such as non-stem cells, adult stem cells and embryonic stem cells.

The various methods employed in the genetic modification of cells are well known in the art and are described, for example, in Sambrook et al. (1989) Molecular Cloning: A Laboratory Manual, second edition, volumes 1 3, Cold Spring Harbor Laboratory, New York, and Gloves, D. M. (1985) DNA Cloning, Vol. I: A Practical Approach, IRL Press, Oxford. Thus, it is within the skill of those in the genetic engineering art to extract DNA from its source, perform restriction enzyme digestions, electrophorese DNA fragments, tail and anneal plasmid and insert DNA, ligate DNA, transform cells, e.g., prokaryotic and eukaryotic cells, prepare plasmid DNA, electrophorese proteins, and sequence DNA.

The cells grown using the invention can range in plasticity from totipotent or pluripotent stem cells (e.g., adult or embryonic), precursor or progenitor cells, to highly specialized cells, such as those of the central nervous system (e.g., neurons and glia). In some embodiments, the cells are bone marrow cells, hematopoietic stem cells or hematopoietic progenitor cells, mesenchymal stem cells, or other stem cells or progenitor cells. The cells may be administered to a subject in an enriched (e.g., purified or isolated) or non-enriched form. Stem and progenitor cells can be obtained from a variety of sources, including embryonic tissue, fetal tissue, adult tissue, umbilical cord blood, peripheral blood, bone marrow, and brain, for example.

In some embodiments, the cells are human cells. However, it will be understood by one of skill in the art that the present invention is also applicable for veterinary purposes. Cells of non-human animals can find application either in human or animal subjects (transplant recipients). For example, although dopamine neurons from human, pig, and rat are similar in that they synthesize dopamine and release synaptically into the brain, they differ immunologically, in extent of reinervation of the brain, in life span, and in infection agents associated with the specific donor or donor species. These traits can be exploited for their specific strengths and weaknesses.

As will be understood by those skilled in the art, there are over 200 cell types in the human body. The production modules, production suites, and methods of the invention can be used to grow any of these cell types. For example, cells can include those cells arising from the ectoderm, mesoderm, or endoderm germ cell layers. Such cells include, but are not limited to, bone marrow cells, neurons, glial cells (astrocytes and oligodendrocytes), muscle cells (e.g., cardiac, skeletal), chondrocytes, fibroblasts, melanocytes, Langerhans cells, keratinocytes, endothelial cells, epithelial cells, pigment cells (e.g., melanocytes, retinal pigment epithelial (RPE) cells, iris pigment epithelial (IPE) cells), hepatocytes, microvascular cells, pericytes (Rouget cells), blood cells (e.g., erythrocytes), cells of the immune system (e.g., B and T lymphocytes, plasma cells, macrophages/monocytes, dendritic cells, neutrophils, eosinophils, mast cells), thyroid cells, parathyroid cells, pituitary cells, pancreatic cells (e.g., insulin-producing beta cells, glucagon-producing alpha cells, somatostatin-producing delta cells, pancreatic polypeptide-producing cells, pancreatic ductal cells), stromal cells, adipocytes, reticular cells, rod cells, and hair cells. Other examples of cell types that can be grown include those disclosed by Spier R. E. et al., eds., (2000) The Encyclopedia of Cell Technology, John Wiley & Sons, Inc., and Alberts B. et al., eds., (1994) Molecular Biology of the Cell, $3^{rd}$ ed., Garland Publishing, Inc., e.g., pages 1188-1189.

Various cell lines have also been used for a variety of purposes, and can be grown using the production modules, production suites, and methods of the invention. Fetal kidney cells and amniotic cells have been transplanted as sources of trophic factors. Adrenal medullary cells, sympathetic ganglion cells, and carotid body cells have been transplanted as sources of dopamine. Fibroblasts and glial cells have been transplanted as sources of trophic factors, to carry genes through recombinant strategies, or for demyelinating diseases, for example. Corneal endothelial cells have been used for corneal transplants. Myoblasts have been transplanted for the treatment of muscular dystrophy and cardiac disease. Other cell lines include pancreatic islet cells for diabetes; thyroid cells for thyroid disorders; blood cells for AIDS, bone marrow transplant, and inherited disorders; bone and cartilage for osteoarthritis, rheumatoid arthritis, or for fracture repair; skin or fat cells for reconstructive purposes, such as in skin grafts after burns or cosmetic surgery; breast augmentation with fat; hair follicle replacement; liver cells for liver disorders inducing hepatitis; and retinal pigment epithelial cells (RPE) for retinitis pigmentosa and Parkinson's disease.

The cells to be used in the various aspects of the present invention are preferably mammalian cells. They may be of human or animal origin. Examples of mammalian cells that can be grown using the production modules, production suites, and methods of the invention include, but are not limited to, murine C127 cells, 3T3 cells, COS cells, human osteosarcoma cells, MRC-5 cells, BHK cells, VERO cells, CHO (Chinese hamster ovary) cells, HEK 293 cells, rHEK 293 cells, normal human fibroblast cells, Stroma cells, Hepatocytes, or PER.C6 cells. Examples of hybridomas that may be cultured in the process according to the present invention include, e.g., DA4.4 cells, 123A cells, 127A cells, GAMMA cells and 67-9-B cells.

Stem cells are believed to have immense potential for therapeutic purposes for numerous diseases. Stem cells have been derived from numerous donor sources, including, but not limited to, embryonic, blast, tissue-derived, blood, and cord-blood cells; organ-derived progenitor cells; and bone marrow stromal cells, among others. Such stem cells can be differentiated along numerous pathways to produce virtually any cell type. These cells can be transplanted either before or after differentiation. Hematopoietic stem cells (HSC) have been used for many years, and typically used for treatment of hematopoietic cancers (e.g., leukemias and lymphomas), non-hematopoietic malignancies (cancers in other organs). Other indications include diseases that involve genetic or acquired bone marrow failure, such as aplastic anemia, thalassemia sickle cell anemia, and autoimmune diseases.

Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001). The list of adult tissues reported to contain stem cells is growing and includes bone marrow, peripheral blood, umbilical cord blood, brain, spinal cord, dental pulp, blood vessels, skeletal muscle, epithelia of the skin and digestive system, cornea, retina, liver, and pancreas.

Optionally, stem cells may be induced to differentiate using various techniques or exposure to agents (differentiation-inducing agents). For example, depending upon the cell type, stem cells may induced to differentiate along certain lineages in cell culture by applying mechanical force (e.g., compressive forces or pressure, tensile forces (e.g., mechanical loading or stretch), and fluid-applied forces (shear flow)), or by contacting the cells with one or more differentiation-inducing agents (e.g., trophic factors, hormonal supplements), such as forskolin, retinoic acid, putrescin-transferrin, cholera toxin, insulin-like growth factor (IGF), transforming growth factor (e.g., TGF-.alpha., TGF-.beta.), tumor necrosis factor (TNF), fibroblast growth factor (FGF), epidermal growth factor (EGF), granulocyte macrophage-colony stimulating factor (GM-CSF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP) phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), leukemia inhibitory factor (LIF), potassium, amphiregulin, dexamethasone (glucocorticoid hormone), isobutyl 3-methylxanthine, somatostatin, lithium, and growth hormone.

Cells and cells-derived products can be harvested using methods known in the art. Various biomolecules produced by genetically modified or non-genetically modified cells that are produced using the production modules, production suites, and methods of the invention can be harvested (e.g., isolated from the biomolecule-producing cells) for various uses, such as the production of drugs and for pharmacological studies. Thus, using the production modules, production suites, and methods of the invention, cells can be used as biological "factories" to provide the product of exogenous DNA and/or the natural product of the cells in vitro, or in vivo within an animal. The term "biomolecule" refers to a molecule or molecules that can be produced by cells (a cell-derived product). Such biomolecules include, but are not limited to, proteins, peptides, amino acids, lipids, carbohydrates, nucleic acids, nucleotides, viruses, and other substances. Some specific examples of biomolecules include trophic factors, hormones, and growth factors, such as brain-derived growth factor (BDNF) and glial-derived neurotrophic factor (GDNF). For example, pituitary cells can be grown to produce growth hormone; kidney cells can be grown to produce plasminogen activator; bone cells can be grown to produce bone morphogenetic protein (BMP) or other proteins involved in bony fusions or prosthetic surgery. Hepatitis-A antigen can be produced from liver cells. Cells can be grown to produce various viral vaccines and antibodies. Interferon, insulin, angiogenic factor, fibronectin and numerous other biomolecules can be produced by growing cells and harvesting these products. The biomolecules can be intracellular, transmembrane, or secreted by the cells, for example.

Cells produced using the invention can be administered to humans or animals as cell therapy to alleviate the symptoms of a wide variety of disease states and pathological conditions, in various stages of pathological development. For example, cells can be used to treat acute disorders (e.g., stroke or myocardial infarction), and administered acutely, subacutely, or in the chronic state. Similarly, the cells of the subject invention can be used to treat chronic disorders (e.g., Parkinson's disease, diabetes, or muscular dystrophy), and administered preventatively and/or prophylactically, early in the disease state, in moderate disease states, or in severe disease states. For example, the cells can be administered to a target site or sites on or within a patient in order to replace or compensate for the patient's own damaged, lost, or otherwise dysfunctional cells. This includes infusion of the cells into the patient's bloodstream. The cells to be administered can be cells of the same cell type as those damaged, lost, or otherwise dysfunctional, or a different cell type. As used herein, patients "in need" of the cells of the subject invention include those desiring elective surgery, such as elective cosmetic surgery.

The cells of the invention can be administered as autografts, syngeneic grafts, allografts, and xenografts, for example. As used herein, the term "graft" refers to one or more cells intended for implantation within a human or non-human animal. Hence, the graft can be a cellular or tissue graft, for example. Cells can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. The cells can be administered to a patient in isolation or within a pharmaceutical composition comprising the cells and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, Remington's Pharmaceutical Science (Martin E. W., Easton Pa., Mack Publishing Company, 19th ed.) describes formulations that can be used in connection with the subject invention. Formulations suitable for parenteral administration, for example, include aqueous sterile injection solutions, which may contain antioxidants, buffers, bacteriostats, and solutes that render the formulation isotonic with the blood of the intended recipient; and aqueous and nonaqueous sterile suspensions that may include suspending agents and thickening agents. It should be understood that in addition to the ingredients particularly mentioned above, the formulations of the subject invention can include other agents conventional in the art having regard to the type of formulation and route of administration in question.

IV. POLYPEPTIDE PRODUCTION

The biomolecule can be a polypeptide of interest, such as a naturally secreted protein, a normally cytoplasmic protein, a normally transmembrane protein, or a human or a humanized antibody. When the protein of interest is a naturally cytoplasmic or a naturally transmembrane protein, the protein has preferably been engineered in order to become soluble and secreted, i.e., by placing a signal peptide in front of it or of a (soluble or extracellular) fragment of it. However, intracellular biomolecules may also be harvested by lysing the cells.

The polypeptide of interest may be of any origin. Some polypeptides of interest are of human origin, and may be therapeutic proteins. For example, the protein of interest may be selected from a hormone, a cytokine-binding protein, an interferon, a soluble receptor, or an antibody. Therapeutic proteins that may be produced include, for example, chorionic gonadotropin, follicle-stimulating hormone, lutropin-choriogonadotropic hormone, thyroid stimulating hormone, growth hormone, in particular human growth hormone, interferons (e.g., interferon beta-1a, interferon beta-1b), interferon receptors (e.g., interferon gamma receptor), TNF receptors p55 and p75, and soluble versions thereof, TACI receptor and Fc fusion proteins thereof, interleukins (e.g., interleukin-2, interleukin-11), interleukin binding proteins (e.g., interleukin-18 binding protein), anti-CD11a antibodies, erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof. In some embodiments, the polypeptide is selected from the group consisting of chorionic gonadotropin (CG), follicle-stimulating hormone (FSH), lutropin-choriogonadotropic hormone (LH), thyroid stimulating hormone (TSH), human growth hormone (hGH), interferons (e.g., interferon beta-1a, interferon beta-1b), interferon receptors (e.g., interferon gamma receptor), TNF receptors p55 and p75, interleukins (e.g., interleukin-2, interleukin-11), interleukin binding proteins (e.g., interleukin-18 binding protein), anti-CD11a antibodies, and muteins, fragments, soluble forms, functional derivatives, fusion proteins thereof.

Further preferred polypeptides of interest include, e.g., erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

Proteins that can be produced by the present invention include tumor antigens and antibodies. An epitope of the tumor antigen can be any site on the antigen that is reactive with an antibody or T cell receptor. Other examples of tumor antigens include, but are not limited to human epithelial cell mucin (Muc-1; a 20 amino acid core repeat for Muc-1 glycoprotein, present on breast cancer cells and pancreatic cancer cells), the Ha-ras oncogene product, p53, carcinoembryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7 and melanoma gangliosides, as well as any other tumor antigens now known or identified in the future. In some embodiments, the tumor antigen is the idiotype of a B-cell derived lymphoma (e.g., IgM or IgG isotype). Various antibody isotypes may be produced using the invention, including IgG, IgM, IgA, IgD, and IgE. In some embodiments, the product is an antibody, which may then be conjugated to a carrier molecule, such as a carrier protein (e.g., keyhole limpet hemocyanin (KLH)).

The subject invention provides a ready source of polypeptides for medicine and research. Polypeptides produced using the invention can be administered to a human or non-human animal by any method of delivery, such as intravascularly, intracranially, intracerebrally, intramuscularly, intradermally, intravenously, intraocularly, orally, nasally, topically, or by open surgical procedure, depending upon the anatomical site or sites to which the polypeptides are to be delivered. The polypeptides can be administered to a patient in isolation or within a pharmaceutical composition comprising the polypeptide and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, Remington's Pharmaceutical Science (Martin E. W., Easton Pa., Mack Publishing Company, 19th ed.) describes formulations that can be used in connection with the subject invention. Formulations suitable for parenteral administration, for example, include aqueous sterile injection solutions, which may contain antioxidants, buffers, bacteriostats, and solutes that render the formulation isotonic with the blood of the intended recipient; and aqueous and nonaqueous sterile suspensions that may include suspending agents and thickening agents. It should be understood that in addition to the ingredients particularly mentioned above, the formulations of the subject invention can include other agents conventional in the art having regard to the type of formulation and route of administration in question.

V. VIRUS AND VIRUS-LIKE PARTICLE PRODUCTION

Viruses, virus-like particles (VLP), and viral vectors represent another type of cell-derived product that may be produced using the production modules, production suites, and methods of the invention. Viruses, VLPs, and viral vectors can be produced with the invention using cell types utilized for propagating the virus of interest. Examples of mammalian cells useful for production of virus include Madin-Darby canine kidney (MDCK) cells, VERO cells, or other monolayer cell types. The cells are grown in the bioreactor of the invention and, after a sufficient cell number is reached, can then be infected with the virus or viral vector, which spreads throughout the culture and larger quantities of virus or vector is then harvested. Alternatively, cells can be infected prior to inoculation of the bioreactor with the cells. The harvested virus and vectors can be used, for example, for vaccines and/or as gene delivery vectors. For example, influenza virus can be grown and vaccines for influenza produced from the harvested virus. While the roller-bottle and egg-based vaccine production processes remain relatively reliable, an efficient cell-based production system would represent a significant improvement in providing a faster, less-expensive, and less cumbersome method of growing viruses.

Madin-Darby canine kidney (MDCK) cells and African green monkey kidney (Vero) cells are useful for the production of influenza virus. Other continuous cell lines suitable as host cells for production of human vaccines include human fetal retina (Per.C6) and duck embryonic retina (AGE1.CR) cells. In addition to production of virus, the invention may be used for growth and expansion of virus-infected cells, and cell culture-based production of viruses products, e.g., production of virus, viral vaccines, viral proteins, viral vectors for gene delivery, and VLPs.

In some embodiments, the virus is influenza A, B or C. In some embodiments, the virus is influenza A strain H5N1 or H1N1. In some embodiments, the virus is an orthomyxovirus, paramyxovirus, arbovirus, filovirus, enterovirus, rhinovirus, herpes virus, or hepadina virus.

The methods for production of virus (including viral vectors) and VLPs involving culturing the virus-infected cells under conditions that allow for regulation of the concentration of a molecule inhibitory to virus or VLP yield (such as non-structural (NS) protein, viral ribnucleoprotein (RNP), etc.), as described in WO 2012/171026 (Hirschel et al., "Methods for High Yield Virus Production", published Dec. 13, 2012), which is incorporated herein by reference in its entirety, may be utilized with this invention. In an embodiment, these methods for the production of virus and VLP comprise culturing virus-infected cells in a bioreactor comprising a first compartment, a second compartment, and a membrane separating the first and second compartments, wherein the cells are cultured in the first compartment under conditions that allow for regulating the concentration of a molecule inhibitory to virus or VLP yield from the cells within the first compartment, and allow for production of the virus or VLP at a yield greater than that achieved in the absence of said regulation. In another embodiment, the method involves regulating the concentration of a molecule inhibitory to viral yield or VLP yield in a first compartment of a bioreactor comprising the first compartment, a second compartment, and a membrane separating the first and second compartments, the method comprising the culturing virus-infected cells in the first compartment by adding cell culture medium to the first compartment and controlling how rapidly culture medium bearing the inhibitor molecule is replaced with fresh culture medium in the first compartment, or by diffusing one or more inhibitor molecules from the first compartment, through the membrane, into the second compartment.

The following is an example of a cell culture run for virus production. An operator removes the sterile cultureware from its packaging and mounts it to the instrument module. Mechanical interfacing occurs automatically when the cultureware is inserted. Cultureware module information is scanned by the instrument and stored for the batch record. Sterile connections are made to the defined media source, waste factor and harvest (FIG. 5) vessels. The operator starts the process and the instrument automatically sequences through the process of flushing and preparing the cultureware module for inoculation. Throughout the run, online intercapillary metabolic analysis (FIG. 5) can be used to verify the sensor array and provide additional information to the instrument. Just before inoculation, factor supplemented media is introduced into the extracapillary space. Once prepared, MDCK (Madin-Darby Canine Kidney) cells or other host cells appropriate for production of the virus can be introduced locally through the Inoculum-In (pumped into the bioreactors) or diverted from neighboring cultureware modules (FIGS. 4 and 5). The instrument sequence shifts into a growth mode to expand the cell mass. Medium is perfused through the bioreactors of the cultureware module. This serves to deliver nutrients to the cell space and conversely, removes or prevents a toxic build-up of metabolic waste. During this circulation, medium is passed through an oxygenator or gas exchanger cartridge (FIGS. 3 and 5) which serves to provide control and oxygen for the cells and conversely, remove carbon dioxide from the culture. When the bioreactor contains a smaller number of cells (e.g., immediately after inoculation), the oxygenator or gas exchange cartridge can be used to provide $CO_2$ and subsequently control pH of the culture environment using the sensors built into the cultureware module (FIG. 5). As cell number increases, the oxygenator is used to remove $CO_2$ which serves to enhance acid neutralization and control the pH of the culture. The online extracapillary biochemical analysis (FIG. 5) provides information concerning the product concentration or cell mass. After a number of days when the cell mass is determined to be optimal, the operator will initiate introduction of virus and/or virus-infected cells (e.g., Influenza virus and/or Influenza infected cells) into the cell mass locally through the Inoculum-In (pumped into the bioreactors) or diverted from neighboring infected cultureware modules (FIGS. 4 and 5). After an infection period, harvesting of the infectious (plaque-forming) virus is started, which can be locally from the harvest line or network-wide from the Inoculum-Out line. When a significant drop in one or more metabolics is observed, harvesting is stopped. The operator removes the harvest, if local, and indicates the run is complete. The instrument module prepares for cultureware removal. Sterile disconnects are made for the inoculum, media and waste lines. The cultureware module is removed and preferably disposed of as a biological hazard. The instrument module surfaces can be spray cleaned. The instrument is then ready for the next production run.

The process of manufacturing a viral vaccine comprises the process of replicating a virus using a production module, production suite, and/or method of the invention and harvesting the virus or VLP, which can include at least one step selected among filtering, concentrating, freezing and stabilizing by addition of a stabilizing agent. The virus harvest can be performed according to technologies well-known to the man skilled in the art. According to a preferred embodiment, the step of harvesting the virus comprises collecting cell culture supernatant obtained from centrifugation, then filtering, concentrating, freezing and stabilizing virus preparation by addition of stabilizing agent. For example, for influenza virus, see Furminger, In Nicholson, Webster and Hay (Eds) Textbook of influenza, chapter 24 pp 324-332.

The process of manufacturing a viral vaccine according to the invention may also comprise the additional step of inactivation of harvested virus. Inactivation can be performed by treatment with formaldehyde, beta-propiolactone, ether, ether and detergent (i.e., such as Tween 80™), cetyl-trimethyl ammonium bromide (CTAB) and Triton N102, sodium deoxycholate and tri(N-butyl)phosphate.

The production module, production suite, and methods of the invention may also be used for preparation of viral antigenic proteins from the virus produced therewith. The method further comprises the additional steps of: a) optionally, incubating cell culture supernatant comprising whole virus harvested from the bioreactor with a desoxyribonucleic acid restriction enzyme, preferably DNAses and nucleases (preferably, the DNA digestion enzyme is benzonase (Benzon nuclease) or DNase I); b) adjunction of cationic detergent (examples of cationic detergent are; without limitation: cetyl-trimethyl ammonium salt such as CTAB, myristyl-trimethyl ammonium salt, lipofectine, DOTMA and Tween™); c) isolation of antigenic proteins. This later step may be carried out by centrifugation or ultrafiltration.

The virus in the vaccine may be present either as intact virus particles, or as disintegrated virus particles. According to an embodiment, the vaccine is a killed or inactivated vaccine. According to another embodiment, the vaccine is a live attenuated vaccine. According to a third embodiment, the vaccine comprises viral antigenic proteins obtainable from a virus prepared according to the method of the invention.

The vaccine may comprise the virus in combination with pharmaceutically acceptable substances which increase the immune response. Non-limiting examples of substances which increase the immune response comprises incomplete Freund adjuvant, saponine, aluminium hydroxide salts, lysolecithin, plutonic polyols, polyanions, peptides, bacilli Calmette-Guerin (BCG) and *corynebacterium parvum*. In addition, immuno-stimulating proteins (e.g., interleukins IL-1, IL-2, IL-3, IL-4, IL-12, IL-13, granulocyte-macrophage-colony-stimulating factor) may be used to enhance the vaccine immune response.

The vaccine may be a liquid formulation, a frozen preparation, a dehydrated and frozen preparation, or adapted to intra-nasal route of administration, for example.

The vaccine may be used for the prophylactic and/or therapeutic treatment of a human infected by a virus or at risk of infection, or for treatment or prevention of other diseases such as cancer. The viral vaccine may be a recombinant viral vaccine.

The subject invention provides a ready source of vaccines for medicine and research. Vaccines produced using the invention can be administered to a human or non-human animal by any method of delivery, such as intravascularly, intracranially, intracerebrally, intramuscularly, intradermally, intravenously, intraocularly, orally, nasally, or topically, depending upon the anatomical site or sites to which the vaccines are to be delivered. The vaccines can be administered to a patient in isolation or within a pharmaceutical composition comprising the vaccine and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, Remington's Pharmaceutical Science (Martin E. W., Easton Pa., Mack Publishing Company, 19th ed.) describes formulations that can be used in connection with the subject invention. Formulations suitable for parenteral administration, for example, include aqueous sterile injection solutions, which may contain antioxidants, buffers, bacteriostats, and solutes that render the formulation isotonic with the blood of the intended recipient; and aqueous and nonaqueous sterile suspensions that may include suspending agents and thickening agents. It should be understood that in addition to the ingredients particularly mentioned above, the formulations of the subject invention can include other agents conventional in the art having regard to the type of formulation and route of administration in question.

VI. COMPUTER IMPLEMENTATION AND COMPUTER READABLE MEDIA

Aspects of the invention can be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, formats, and numerous other details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention can be practiced without these specific details. Computer systems, servers, work stations, and other machines can be connected to one another across a communication medium including, for example, a network or networks.

As one skilled in the art will appreciate, embodiments of the present invention can be embodied as, among other things: a method, system, or computer-program product. Accordingly, the embodiments can take the form of a hardware embodiment, a software embodiment, or an embodiment combining software and hardware. In an embodiment, the present invention takes the form of a computer-program product that includes computer-useable instructions embodied on one or more computer-readable media. Methods, data structures, interfaces, and other aspects of the invention described above can be embodied in such a computer-program product.

Software can provide for sequenced operation of an individual production module or a group of functionally connected production modules (a production suite). System security (operator identification, password protection, multi-tiered users, alarm notification and operational tog for batch record) can be provided. Transactional interaction with a Manufacturing Execution System (MES) is supported. In one embodiment, the software provides sequenced operation that includes one or more (and preferably all) of the following modes or phases comprising the described steps or operation status:

Idle—non-running state. Optionally, during the idle mode, access to historical data, calibration and test.

Load—Mounting of the cultureware module onto the instrument module.

Acceptance Testing—checking the integrity of the loaded cultureware module,

Flush—Filling fluid and exchanging additional volume to purge wetting components from the bioreactors.

Pre-inoculation—circulating fluid and stabilizing cultureware operation. Optionally, range testing of sensing elements can be performed during the pre-inoculation mode. Factors can be introduced at the end of this step.

Inoculation—Moving inoculum cells and/or virus) from source (e.g., from a local container or networked from another production module).

Growth—Modifying the cell culture environment by manipulating/maintaining pH, circulation flow, media feed, factor addition, EC fluid removal and EC fluid cycling to optimize cell mass increase or productivity. This can be based on sensor readings (on-line and off-line), a pre-determined sequence or a combination of both (sequence held until defined readings are observed).

Harvest—harvesting of product may be a one-time individual event (e.g., infection—infection amplification period—harvest), multiple occurrences, or continuous, triggered sometime after growth starts.

Unload—Un-mounting of the cultureware module from the instrument module.

Computer-readable media include both volatile and nonvolatile media, removable and nonremovable media, and contemplate media readable by a database, a switch, and various other network devices. By way of example, and not limitation, computer-readable media incorporate media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments or modules to initiate a variety of tasks in response to data received in conjunction with the source of the received data.

The present invention can be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop, laptop, or tablet computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touch-pad, touch-screen, or other pointing device, a keyboard, a camera, a monitor, a microphone, a speaker, a printer, a scanner, among other such devices. As further discussed above, the client devices can support various styles and types of client applications.

Thus, one aspect of the invention provides one or more computer-readable media having computer-useable instructions embodied thereon for performing the method for large-scale production of cells and/or cell-derived products. In some embodiments, the steps of the method are performed by one or more suitably programmed computers. In some embodiments, the computer executable instructions for performing one or more of the steps of the method are provided on the one or more computer readable media. In some embodiments, the computer executable instructions are provided as one or more program modules, such as routines, programs, objects, components, and/or data structures. The computer-readable media are non-transitory computer readable, which includes all computer-readable except for a transitory propagating signal. Thus, a non-transitory computer readable medium includes a hard drive, compact disc, DVD, flash memory, USB drive, volatile memory, and a memory card, but does not include a transitory signal per se. Accordingly, the term "non-transitory" is not intended to exclude computer readable media such as a volatile memory or RAM, where the data stored thereon is only temporarily stored, or stored in a "transitory" fashion.

VII. EXEMPLIFIED EMBODIMENTS

The following are exemplified embodiments.

Embodiment 1

A production module for production of cells and/or cell-derived products, comprising: (a) a cultureware module comprising one or more bioreactors and an interface plate with the one or more bioreactors mounted thereto; and (b) an instrument module comprising hardware to support cell culture growth, wherein said instrument module and said cultureware module are adapted for removable attachment to one another.

Embodiment 2

The production module of embodiment 1, wherein said cultureware module comprises a plurality of bioreactors.

Embodiment 3

The production module of embodiment 2, wherein the plurality of bioreactors are connected (in fluid communication) by a flow path that permits inoculation of one or more bioreactors in the plurality to result in inoculation of one or more other ("downstream") bioreactors in the plurality.

Embodiment 4

The production module of any one of embodiments 1 to 3, wherein the one or more bioreactors are hollow-fiber bioreactors.

Embodiment 5

A production suite comprising a plurality of production modules of any one of embodiments 1 to 4, functionally connected.

Embodiment 6

The production suite of embodiment 5, wherein the plurality of production modules are connected (in fluid communication) by a flow path that permits inoculation of one or more production modules in the plurality of production modules to result in inoculation of one or more other ("downstream") production modules in the plurality of production modules.

Embodiment 7

The production suite of embodiment 5, further comprising a room with one or more support surfaces for supporting the plurality of production modules.

Embodiment 8

The production suite of any one of embodiments 5 to 7, wherein the room is environment-controlled (e.g., temperature controlled and/or humidity controlled, etc.).

Embodiment 9

The production suite of embodiment 7 or 8, wherein the room is a modular and/or relocatable building.

Embodiment 10

The production suite of embodiment 9, further comprising one or more receivers affixed to the building frame or wall, for receiving a lifting attachment allowing transport of the building onto a truck, trailer, vessel, aircraft, or other conveyance.

Embodiment 11

The production suite of any one of embodiments 7 to 10, wherein the room includes environmental filtration and containment to an extent necessary for the cell or cell-derived product.

Embodiment 12

The production suite of any one of embodiments 7 to 11, wherein the room has controlled ingress and egress (e.g., to a gowning area).

Embodiment 13

The production suite of any one of embodiments 7 to 12, wherein the room has external control and monitoring stations to allow an operator to check or make adjustments in the operation of the production suite.

Embodiment 14

The production suite of any one of embodiments 7 to 13, wherein the room further comprises one or more video monitoring devices for monitoring the production modules of the production suite.

Embodiment 15

A method for large-scale production of cells and/or cell-derived products, comprising providing one or more production modules or one or more production suites of any preceding embodiment, introducing cells into the one or more bioreactors; culturing the cells to produce grown cells and/or cell-derived products; and harvesting the grown cells and/or cell-derived products.

Embodiment 16

The method of embodiment 15, wherein the cells are mammalian cells, insect cells, avian cells, or plant cells.

Embodiment 17

The method of embodiment 15, wherein the cells are selected from among Madin-Darby canine kidney (MDCK) cells, African green monkey kidney (Vero) cells, human fetal retina (Per.C6) cells, duck embryonic retina (AGE1.CR) cells, murine C127 cells, 3T3 cells, COS cells, human osteosarcoma cells, MRC-5 cells, BHK cells, CHO (Chinese hamster ovary) cells, HEK 293 cells, rHEK 293 cells, human fibroblast cells, stroma cells, or hepatocytes.

Embodiment 18

The method of any one of embodiments 15 or 17, wherein the cell-derived products are selected from among immunoglobulins, proteins, virus, and virus-like particles.

Embodiment 19

One or more computer-readable media having computer-useable instructions embodied thereon for performing the method of any one of embodiments 15-18.

Embodiment 20

The media of embodiment 19, wherein one or more of the steps of the method are performed by one or more suitably programmed computers.

Embodiment 21

The media of embodiment 20, wherein computer executable instructions for performing one or more of the steps of the method are provided on the one or more computer readable media.

Embodiment 22

The media of embodiment 21, wherein the computer executable instructions are provided as one or more program modules.

Embodiment 23

The media of embodiment 22, wherein the program modules include routines, programs, objects, components, and/or data structures.

Embodiment 24

The media of embodiment of any one of embodiments 19 to 23, wherein the media includes one, two, three, four, five, six, seven, eight, or nine of the following modes: idle, load, acceptance testing, flush, pre-inoculation, inoculation, growth, harvest, and unload.

Embodiment 25

The media of embodiment 24, wherein the media includes each of the following modes: idle, load, acceptance testing, flush, pre-inoculation, inoculation, growth, harvest, and unload.

VIII. DEFINITIONS

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a cultureware module" is inclusive of more than one cultureware module, reference to "a bioreactor" is inclusive of more than one bioreactor, and the like.

As used herein, the terms "comprising", "consisting of" and "consisting essentially of" are defined according to their standard meaning. The terms may be substituted for one another herein in order to attach the specific meaning associated with each term.

The term "virus," is used interchangeably herein with fragment or portion of viruses (e.g., virus-like particles (VLPs)). Thus, the term "virus" is inclusive of viruses and viral particles. Any virus may potentially be produced and purified using the bioreactor, apparatus, and methods of the invention. The selection of virus is only limited by the availability of a suitable host cell for production. Virus may be lytic virus or budding virus. Virus may be enveloped or naked virus. For example, orthomyxovirus (e.g., influenza virus A, B, and C), paramyxovirus (e.g., measles, respiratory syncytial virus), arbovirus (e.g., Dengue virus), filovirus (e.g., Ebola), enterovirus (e.g., polio virus), rhinovirus, herpes virus, and hepadina virus can be produced and purified. In some embodiments, the virus is a non-human animal virus. In some embodiments, the virus is a human virus, such as human influenza virus (e.g., strains H5N1 and H1N1).

As used herein, the terms "automation" and "automated" are used interchangeably and refer to the controlled operation of an apparatus, process, or system by mechanical or electronic devices. Automated methods of the invention include sequential, pre-determined steps, which are internally controlled by software driven servo-actuators. Thus, the methods are standardized, efficient, and free of human error.

As used herein, the term "computer system" generally includes one or more computers, peripheral equipment, and software that perform data processing. A "user" or "operator" in general includes a person that utilizes the apparatus of the invention such as through a user interface. A "computer" is generally a functional unit that can perform substantial computations, including numerous arithmetic operations and logic operations without human intervention.

As used herein, the term "culture" is used to denote the maintenance or cultivation of cells in vitro including the culture of single cells. Cultures can be cell, tissue, or organ cultures, depending upon the extent of organization. Cells may be cultured in a bioreactor. The intended product of the cell culture may be the cells themselves, or biomolecules produced by the cells, or virus, VLPs, or viral vectors produced by the cells, or a combination of two or more of the foregoing.

As used herein, "cultureware" refers to components which come in contact with cell or cell-derived product-containing medium, the purified or unpurified product, or any liquid involved in the cell culture and/or purification process.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for large-scale production of cells and/or cell-derived products, comprising:
  providing one or more production modules,
  wherein each of the one or more production modules comprises:
   (a) a cultureware module comprising a plurality of hollow-fiber bioreactors, an intracapillary reservoir, an extracapillary reservoir, and an interface plate with said plurality of hollow-fiber bioreactors mounted thereto, wherein each hollow-fiber bioreactor has an intracapillary space and an extracapillary space, and wherein each hollow-fiber bioreactor is connected to an adjacent hollow-fiber bioreactor by a flow path; and
   an instrument module comprising a pump for circulating cell culture medium through the plurality of hollow-fiber bioreactors, an intracapillary manifold connected to the intracapillary space and the intracapillary reservoir, an extracapillary manifold connected to the extracapillary space and the extracapillary reservoir, wherein the instrument module and the cultureware module are adapted for removable attachment to one another;
  introducing cells into one or more of the hollow-fiber bioreactors;
  culturing the cells to produce grown cells and/or cell-derived products; and
  harvesting the grown cells and/or cell-derived products.

2. The method of claim 1, wherein the cells are mammalian cells, insect cells, avian cells, or plant cells.

3. The method of claim 1, wherein the cells are selected from among Madin-Darby canine kidney (MDCK) cells, African green monkey kidney (Vero) cells, human fetal retina (Per.C6) cells, duck embryonic retina (AGE1.CR) cells, murine C127 cells, 3T3 cells, COS cells, human osteosarcoma cells, MRC-5 cells, BHK cells, CHO (Chinese hamster ovary) cells, HEK 293 cells, rHEK 293 cells, human fibroblast cells, stroma cells, or hepatocytes.

4. The method of claim 1, wherein the cell-derived products are selected from among immunoglobulins, proteins, virus, and virus-like particles.

5. The method of claim 1, wherein said providing one or more production modules comprises providing one or more production suites, wherein the production suite comprises a plurality of production modules, and wherein each production module of each production suite is functionally connected.

6. The method of claim 5, further comprising providing a room with one or more support surfaces for supporting the plurality of production modules.

7. The method of claim 6, wherein the room is environment-controlled.

8. The method of claim 6, wherein the room includes environmental filtration and containment to an extent necessary for the cell or cell-derived product.

9. The method of claim 6, wherein the room is a modular and/or relocatable building.

10. The method of claim 9, wherein the modular and/or relocatable building further comprises one or more receivers affixed to the building frame or wall, for receiving a lifting attachment, allowing transport of the building onto a truck, trailer, vessel, aircraft, or other conveyance.

11. The method of claim 6, wherein the room has external control and monitoring stations to allow an operator to check or make adjustments in the operation of the production suite.

12. The method of claim 6, wherein the room further comprises one or more video monitoring devices for monitoring the production modules of the production suite.

13. The method of claim 6, wherein the room has controlled ingress and egress.

14. The method of claim 1, wherein the flow path connecting adjacent hollow-fiber bioreactor permits inoculation of one or more hollow-fiber bioreactors in the plurality to result in inoculation of one or more other hollow-fiber bioreactors in the plurality.

* * * * *